(12) United States Patent
Kwiatkowski et al.

(10) Patent No.: US 8,575,320 B2
(45) Date of Patent: Nov. 5, 2013

(54) COMPOSITIONS AND METHODS FOR SEPARATING, CHARACTERIZING AND ADMINISTERING SOLUBLE SELENOGLYCOPROTEINS

(75) Inventors: Stefan Kwiatkowski, Lexington, KY (US); Ronan Power, Lexington, KY (US); Clayton Matney, Nicholasville, KY (US); Paiman Peter Ghoroghchian, Downingtown, PA (US); Eric Michael Ostertag, Lexington, KY (US)

(73) Assignee: Alltech, Inc., Nicholasville, KY (US)

( * ) Notice: Subject to any disclaimer, the term of this patent is extended or adjusted under 35 U.S.C. 154(b) by 0 days.

(21) Appl. No.: 13/235,191

(22) Filed: Sep. 16, 2011

(65) Prior Publication Data

US 2012/0164234 A1 Jun. 28, 2012

Related U.S. Application Data

(63) Continuation-in-part of application No. 13/051,646, filed on Mar. 18, 2011, now Pat. No. 8,263,752.

(60) Provisional application No. 61/315,265, filed on Mar. 18, 2010.

(51) Int. Cl.
*C07K 1/00* (2006.01)
*A61K 36/06* (2006.01)

(52) U.S. Cl.
USPC .......................................... 530/395; 530/371

(58) Field of Classification Search
None
See application file for complete search history.

(56) References Cited

U.S. PATENT DOCUMENTS

| | | | |
|---|---|---|---|
| 5,221,545 | A | 6/1993 | Borschel |
| 5,959,050 | A | 9/1999 | Mosbach |
| 6,197,295 | B1 | 3/2001 | Hsia |
| 6,576,233 | B2 | 6/2003 | Hsia |
| 6,835,394 | B1 | 12/2004 | Discher |
| 6,911,550 | B2 | 6/2005 | Abdel-Monem |
| 7,498,045 | B2 | 3/2009 | Chang |
| 7,682,603 | B2 | 3/2010 | Hammer |
| 7,867,512 | B2 | 1/2011 | Discher |
| 2001/0043925 | A1 | 11/2001 | Hsia |
| 2004/0254239 | A1 | 12/2004 | Abdel-Monem |
| 2005/0019265 | A1 | 1/2005 | Hammer |
| 2005/0069594 | A1 | 3/2005 | Lubinski |
| 2005/0089530 | A1 | 4/2005 | Moesgaard |
| 2005/0123617 | A1 | 6/2005 | Chang |
| 2006/0263415 | A1 | 11/2006 | Sedmak |
| 2007/0077238 | A1 | 4/2007 | Teo et al. |
| 2007/0218123 | A1 | 9/2007 | Discher |
| 2008/0107755 | A1 | 5/2008 | Lyons |
| 2009/0214419 | A1 | 8/2009 | Therien et al. |

OTHER PUBLICATIONS

Mostert et al., "A Novel Method for the Purification of Selenoprotein P from Human Plasma", Archives of Biochemistry and Biophysics, vol. 357, No. 2, Sep. 15, pp. 326-330, 1998.*
Tastet et al., "Identification of selenium-containing proteins in selenium-rich yeast aqueous extract by 2D gel electrophoresis, nanoHPLC—ICP MS and nanoHPLC—ESI MS/MS", Talanta, vol. 75, (2008), pp. 1140-1145.*
Andersson, et al., Molecular Interactions in Bioseparations (Ngo. T. T. ed.), pp. 383-394 (book).
Bedwal, R. S. et al, "Selenium—its biological perspectives", Medical Hypotheses vol. 41, No. 2, Aug. 1993, pp. 150-159.
Brooks et al., "Plasma selenium level before diagnosis and the risk of prostate cancer development." J UROL vol. 166, 2001, pp. 2034-2038.
Clark et al., "Effects of selenium supplementation for cancer prevention in patients with carcinoma of the skin. A randomized controlled trial. Nutritional Prevention of Cancer Study Group" J Am Med Assoc vol. 276, 1996, pp. 1957-1963.
Combs, G.F.; Grey, W.P. 'Chemopreventive Agents: Selenium' Pharmacol. Ther. 79, 179-192 (1998).
Couvreur et al., Nanocapsule technology: a review, Crit Rev Ther Drug Carrier Syst. 2002;19(2):99-134.
Deleve; Kaplowitz, "Glutathione metabolism and its role in hepatotoxicity" Pharm. Ther. vol. 52, 1991, pp. 287-305.
Demirci et al., Enhanced organically bound selenium yeast production by fed-batch fermentation, J Agric Food Chem. Jun. 1999;47(6):2496-500.
Demirci et al., Production of organically bound selenium yeast by continuous fermentation, J Agric Food Chem. Jun. 1999;47(6):2491-5.
Discher et al. Journal of Physical Chemistry B (2002), 106(11), 2848-2854.
El-Bayoumy, K. (1991) The role of selenium in cancer prevention. In: Cancer Principles and Practice of Oncology (DeVita, V. T., Hellman, S. & Rosenberg, S. S., eds.), 4th ed., pp. 1-15. J. B. Lippincott, Philadelphia, PA.
Ferris G. M. Lloyd et al. "The effect of supplementation with selenium and vitamin E in psoriasis" App. Clin. Biochem. vol. 26, 1989, pp. 83-88.
Furnsinn et al., "Improved glucose tolerance by acute vanadate but not by selenate exposure in genetically obese rats (fa/fa)" Int. J of Obesity and Related Metab. Dis. vol. 19, No. 7, 1995, pp. 458-463.

(Continued)

*Primary Examiner* — Suzanne M Noakes
(74) *Attorney, Agent, or Firm* — Casimir Jones S.C.; Tyler J. Sisk

(57) ABSTRACT

The invention relates to soluble selenium compositions and methods of production, separation and purification thereof. In particular the present invention provides methods of preparing water soluble selenoglycoproteins (e.g., via extracting selenoglycoproteins from selenium enriched yeast), methods of supplementing a selenium deficient composition via admixing water soluble selenoglycoproteins with the selenium deficient composition, compositions comprising the water soluble selenoglycoproteins and methods of administering the same.

19 Claims, 13 Drawing Sheets

(56) References Cited

OTHER PUBLICATIONS

Garland et al., "Antioxidant micronutrients and breast cancer" J. Am. Coll Nutr. vol. 12, 1993, pp. 400-411.
Gerloff et al., "Effect of selenium supplementation on dairy cattle" J. Anim. Sci. vol. 70, 1992, pp. 3934-3940.
Ghadirian et al., "A case-control study of toenail selenium and cancer of the breast, colon, and Prostate" Cancer Detect Prev vol. 24, 2000, pp. 305-313.
Ghoroghchian et al., Bioresorbable Vesicles Formed through Spontaneous Self-Assembly of Amphiphilic Poly(ethylene oxide)-block-polycaprolactone, Macromolecules. Mar. 7, 2006;39(5)1673-1675.
Goehring et al., Effects of seleniferous grains and inorganic selenium on tissue and blood composition and growth performance of rats and swine, J Anim Sci. Sep. 1984;59(3):725-32.
IP; Daniel, "Effects of selenium on 7,12-dimethylbenz(a)anthracene-induced mammary carcinogenesis and DNA adduct formation" Cancer Res. vol. 45, 1985, pp. 61-65.
IP, "Lessons from basic research in selenium and cancer prevention" J. Nutr. vol. 128, 1998, pp. 1845-1854.
Kelly, M. P.; Power R. F. 'Fractionation and identification of the major selenium compounds in selenized yeast' J. Dairy Sci. 78, 237-242 (1995).
Korhola.M.; Vainio, A.; Edaelman, K. 'Selenium yeast' Ann. Clin. Res. 18, 65-68, (1986).
Mahan, D.C. 1999. Organic selenium: using nature's model to redefine selenium supplementation for animals. In: Biotechnology in the Feed Industry. Proc. 15th Annual Symposium (T.P. Lyons and K.A. Jacques, eds.). Nottingham University Press, Nottingham, UK, pp. 523-535.
McKenzie, R.C.; Rafferty, T.S.; Beckett, G.J. 'Selenium: an essential element for immune function' Trends in Immunology 19, 342-345 (1998).
McSheehy, S.; Kelly, J.; Tessier, L.; Mester, Z. 'Identification of Selenomethionine in selenized yeast using two-dimentional liquid chromatography-mass spectrometry based proteomic analysis' Analyst 130, 35-37 (2005).
Meister; Anderson, Glutathione, Annual Review of Biochemistry, vol. 52: 711-760 (volume publication date Jul. 1983).
Mosbach. Trends in Biochemical Sciences, vol. 7, pp. 92-96, 1994.
Otero, M.A.; Vasallo, M.C.; Verdecia, O.; Fernandez, V.; Betancourt, D. 'A Process for the Complete Fractionation of Baker's Yeast' J. Chem. Tech. Biotechnol. 66, 67-71 (1996).
Ouerdane L., Mester Z. 'Production and Characterization of Fully Selenomethionine-Labelled *Saccharomyces cerevisiae*' J.Agric. Food Chem. 56,11792-11799, (2008).
Palmer; Paulson, "Reactive oxygen species and antioxidants in signal transduction and gene Expression" Nutr. Rev. vol. 55, 1997, pp. 353-361.
Pence et al., Effects of dietary selenium on UVB-induced skin carcinogenesis and epidermal antioxidant status, J Invest Dermatol. May 1994;102(5):759-61.
Rayman, The importance of selenium to human health, Lancet. Jul. 15, 2000;356(9225):233-41.
Roberge, M.T.; Borgerding, A.J.; Finley, J.W. 'Speciation of Selenium Compounds from High Selenium Broccoli is Affected by the Extracting Solution' J.Agric. Food Chem. 51, 4191-4197 (2003).
Salonen et al., "Association between serum selenium and the risk of cancer" Am. J. Epidemiol. vol. 120, 1984, pp. 342-349.
Surai P.F. Natural Antooxidants in Avian Nutrition and Reproduction Nottingham University Press 2002, 234-236 (2002).
Tapiero, H.; Townsend, D.M.; Tew, K.D. 'The antioxidant role of selenium and selenocompounds' Biomedicine&Pharmacotherapy 57, 134-144 (2003).
Virtamo et al., "Serum selenium and risk of cancer. A prospective follow-up of nine years" Cancer vol. 60, 1987, pp. 145-148.
Willett et al., "Prediagnostic serum selenium and risk of cancer" LANCET vol. 2, 1983, pp. 130-134.
Wulff, The role of binding-site interactions in the molecular imprinting of polymers, Trends Biotechnol. Mar. 1993;11(3):85-7.
Yoshizawa et al., "Study of prediagnostic selenium level in toenails and the risk of advanced prostate cancer" J Natl Cancer Inst vol. 90, 1998, pp. 1219-1224.
Yu et al., "Protective role of selenium against hepatitis B virus and primary liver cancer in Qidong" Biol Trace Elem Res vol. 56, 1997, pp. 117-124.
Andersson et al., Mimics of the binding sites of opioid receptors obtained by molecular imprinting of enkephalin and morphine, Proc. Natl. Acad. Sci., vol. 92, pp. 4788-4792, May 1995.
Takahashi et al., "Purification and characterization of human plasma glutathione peroxidase: a selenoglycoprotein distinct from the known cellular enzyme.", Archives of Biochemistry and Biophysics, Aug. 1987, 256(2):677-686.
Rayman, The use of high-selenium yeast to raise selenium status: how does it measure up?, Br. J. Nutr. Oct. 2004, vol. 92, No. 4, pp. 557-573.
Tanner et al., Fungal glycoproteins and their biosynthetic pathway as potential targets for antifungal agents. Acta Biochim. Pol. (1995), vol. 42, No. 4, pp. 505-508.
Kwiatkowski et al., A Study of *Saccharomyces cerevisiae* Cell Wall Glucans. J. Inst. Brew. (2009), vol. 115, No. 2, pp. 151-158.

\* cited by examiner

*White=down-regulated, Gray=no change, Black= up-regulated in relative gene expression.

* p < 0.05

* p < 0.05

* $p < 0.05$

* $p<0.05$

*p<0.05

*p<0.05

*White=down-regulated, Gray=no change, Black= up-regulated in relative gene expression.

SEQUENCE LISTING

<160> NUMBER OF SEQ ID NOS: 10

<210> SEQ ID NO 1
<211> LENGTH: 12
<212> TYPE: PRT
<213> ORGANISM: Sacchoromyces cerevisiae

<400> SEQUENCE: 1

Gly Ser Asp Thr Met Arg Ser Val Ser Pro Ile Arg
1               5                   10

<210> SEQ ID NO 2
<211> LENGTH: 12
<212> TYPE: PRT
<213> ORGANISM: Sacchoromyces cerevisiae
<220> FEATURE:
<221> NAME/KEY: MISC_FEATURE
<222> LOCATION: (5)..(5)
<223> OTHER INFORMATION: The residue at this position is linked to
      selenium

<400> SEQUENCE: 2

Gly Ser Asp Thr Met Arg Ser Val Ser Pro Ile Arg
1               5                   10

<210> SEQ ID NO 3
<211> LENGTH: 6
<212> TYPE: PRT
<213> ORGANISM: Sacchoromyces cerevisiae

<400> SEQUENCE: 3

Ser Gly Met Ser Lys Lys
1               5

<210> SEQ ID NO 4
<211> LENGTH: 6
<212> TYPE: PRT
<213> ORGANISM: Sacchoromyces cerevisiae
<220> FEATURE:
<221> NAME/KEY: MISC_FEATURE
<222> LOCATION: (3)..(3)
<223> OTHER INFORMATION: The residue at this position is linked to
      selenium

<400> SEQUENCE: 4

Ser Gly Met Ser Lys Lys
1               5

<210> SEQ ID NO 5
<211> LENGTH: 17
<212> TYPE: PRT
<213> ORGANISM: Sacchoromyces cerevisiae

<400> SEQUENCE: 5

Glu Val Ile Gly Ile Asp Pro Ser Ser Ala Met Leu Ser Ile Ala Glu
1               5                   10                  15

Lys

<210> SEQ ID NO 6

```
<211> LENGTH: 17
<212> TYPE: PRT
<213> ORGANISM: Sacchoromyces cerevisiae
<220> FEATURE:
<221> NAME/KEY: MISC_FEATURE
<222> LOCATION: (11)..(11)
<223> OTHER INFORMATION: The residue at this position is linked to
      selenium

<400> SEQUENCE: 6

Glu Val Ile Gly Ile Asp Pro Ser Ser Ala Met Leu Ser Ile Ala Glu
1               5                   10                  15

Lys

<210> SEQ ID NO 7
<211> LENGTH: 5
<212> TYPE: PRT
<213> ORGANISM: Sacchoromyces cerevisiae
<220> FEATURE:
<221> NAME/KEY: MISC_FEATURE
<222> LOCATION: (2)..(2)
<223> OTHER INFORMATION: The residue at this position is linked to
      selenium

<400> SEQUENCE: 7

Ala Met Ile Val Arg
1               5

<210> SEQ ID NO 8
<211> LENGTH: 7
<212> TYPE: PRT
<213> ORGANISM: Sacchoromyces cerevisiae
<220> FEATURE:
<221> NAME/KEY: MISC_FEATURE
<222> LOCATION: (3)..(3)
<223> OTHER INFORMATION: The residue at this position is linked to
      selenium

<400> SEQUENCE: 8

Asp Tyr Met Gly Ala Ala Lys
1               5

<210> SEQ ID NO 9
<211> LENGTH: 8
<212> TYPE: PRT
<213> ORGANISM: Sacchoromyces cerevisiae
<220> FEATURE:
<221> NAME/KEY: MISC_FEATURE
<222> LOCATION: (6)..(6)
<223> OTHER INFORMATION: The residue at this position is linked to
      selenium

<400> SEQUENCE: 9

Ser Ile Val Pro Leu Met Asp Arg
1               5

<210> SEQ ID NO 10
<211> LENGTH: 9
<212> TYPE: PRT
<213> ORGANISM: Sacchoromyces cerevisiae
<220> FEATURE:
<221> NAME/KEY: MISC_FEATURE
<222> LOCATION: (1)..(1)
<223> OTHER INFORMATION: The residue at this position is linked to
      selenium

<400> SEQUENCE: 10

Met Gly His Asp Gln Ser Gly Thr Lys
1               5
```

COMPOSITIONS AND METHODS FOR SEPARATING, CHARACTERIZING AND ADMINISTERING SOLUBLE SELENOGLYCOPROTEINS

This application is a Continuation-In-Part of, and claims priority to, U.S. patent application Ser. No. 13/051,646 filed Mar. 18, 2011, which claims priority to U.S. Provisional Patent Application Ser. No. 61/315,265 filed Mar. 18, 2010, each of which is hereby incorporated by reference in its entirety.

FIELD OF THE INVENTION

The present invention relates to soluble selenium compositions and methods of production, separation and purification thereof. In particular the present invention provides methods of preparing water soluble selenoglycoproteins (e.g., via extracting selenoglycoproteins from selenium enriched yeast), methods of supplementing a selenium deficient composition via admixing water soluble selenoglycoproteins with the selenium deficient composition, compositions comprising the water soluble selenoglycoproteins and methods of administering the same.

BACKGROUND OF THE INVENTION

Selenium is a trace element important for proper physiological function in humans. Selenium is ingested through the diet which can have a varying content of selenium.

Selenium is known to play a critical role in sustaining physiologic metabolism, growth, reproductive health, and immunity. Selenium is incorporated into different organic molecules including, for example, amino acids such as 1-selenomethionine, selenocysteine, and selenocystine. Thus, selenium can be a component part of proteins, many of which are of structural importance to the body. Furthermore, selenium is an important ingredient in a number of enzymes which influence metabolism, reproduction, the prevention of cancer, and immune defense in humans (See, e.g., Rayman, M, Lancet 356:233-241 (2000)).

Multiple studies have attempted to reveal potential health benefits resulting from the ingestion of low levels of selenium. For example, low concentrations of an inorganic form of selenium, have shown some potential health benefits (See, e.g., Furnsinn et al., Int. J. of Obesity and Related Metab. Dis., 19, 458-463 (1995)). However, at elevated dosage levels, beneficial effects are reversed and dangerous toxicity is manifested.

Research over the last two decades has suggested that selenium is effective in the reduction of cancer incidence when provided to animals at doses only 5- to 10-fold above nutritional requirement (See, e.g., El-Bayoumy, The role of selenium in cancer prevention, Philadelphia, Lippincott, 1-15, 1991). Chemoprevention studies with selenium in animal model systems have indicated that this element is effective for most, if not all of the organ systems and is protective against carcinogenic effects (See, e.g., El-Bayoumy, The role of selenium in cancer prevention, Philadelphia, Lippincott, 1-15, 1991. Both epidemiological studies and supplementation trials have also supported its efficacy in lowering the incidence of cancers of the liver, colon, prostate and lung (See, e.g., Yu et al. Biol Trace Elem Res, 56: 117-124 (1997); Clark et al., J Am Med Assoc, 276: 1957-1963 (1996); Yoshizawa et al., J Natl Cancer Inst, 90: 1219-1224, (1998); Brooks, et al., J Urol, 166: 2034-2038, (2001)). Other studies have demonstrated no beneficial effect for selenium reduction of cancers (See, e.g., Garland et al., J. Am. Coll Nutr., 12: 400-11 (1993); Ghadirian et al., Cancer Detect Prev, 24: 305-13 (2000)).

Multiple forms of selenium have been examined. These include inorganic selenium such as sodium selenite, and organic sources, including selenium yeast. There is a significant difference between toxicity of inorganic and organic selenium, the inorganic compounds usually being absorbed and utilized less efficiently and also being more toxic than organic sources of selenium.

SUMMARY OF THE INVENTION

The present invention relates to soluble selenium compositions and methods of production, separation and purification thereof. In particular the present invention provides methods of preparing water soluble selenoglycoproteins (e.g., via extracting selenoglycoproteins from selenium enriched yeast), methods of supplementing a selenium deficient composition via admixing water soluble selenoglycoproteins with the selenium deficient composition, compositions comprising the water soluble selenoglycoproteins and methods of administering the same.

Accordingly, in some embodiments, the present invention provides a method for preparation of soluble selenoglycoproteins comprising: providing selenium enriched yeast, exposing the selenium enriched yeast to acidic conditions followed by centrifugation to generate i) a pellet comprising acid insoluble material; and ii) a liquid phase comprising the extract of selenium enriched yeast soluble under the acidic conditions; precipitating selenoglycoproteins from the liquid phase comprising the extract of selenium enriched yeast soluble under the acidic conditions via raising the pH of the liquid phase, and (d) separating the precipitated selenoglycoproteins from the liquid phase. In some embodiments, exposing the selenium enriched yeast to acidic conditions occurs at a temperature greater than room temperature (e.g., greater than about 20-25° C.). The present invention is not limited by the temperature greater than room temperature under which the selenium enriched yeast are exposed to acidic conditions. Indeed, a variety of temperatures may be used including, but not limited to, about 30, 35, 40, 45, 50, 55, 60, 65, 70, 75, 80, 85, 90, 90, 95, 97, 99° C., or hotter). Similarly, the invention is not limited by the acidic conditions under which the selenium enriched yeast are exposed. In some embodiments, the selenium enriched yeast are exposed to conditions wherein the pH is about 6.5, about 6, about 5.5, about 5, about 4.5, about 4, about 3.5, about 3, about 2.5, about 2, about 1.5, about 1, or less. In a preferred embodiment, exposing the selenium enriched yeast to acidic conditions comprises exposure of the selenium enriched yeast to a pH of 1.5. In some embodiments, exposing the selenium enriched yeast to acidic conditions takes place for a certain period of time. The invention is not limited by the amount of time under which the selenium enriched yeast are exposed to acidic conditions. In some embodiments, the selenium enriched yeast are exposed to acidic conditions for about 1, 2, 3, 4, 5, 6, 7, 8, 9, 10, 11, 12, 14, 16, 18, 20, 22, 24 or more hours. In some embodiments, the selenium enriched yeast are exposed to acidic conditions for between one and twenty-four hours. In some embodiments, the selenium enriched yeast are exposed to acidic conditions for between five and ten hours. In a preferred embodiment, the selenium enriched yeast are exposed to acidic conditions for about eight hours. In some embodiments, acidic conditions are created and/or maintained utilizing acidic buffer and/or the addition of an acid. The invention is not limited by the type of acid utilized. Indeed, any acid may be used. In some embodiments, the acid is hydrochloric acid, although any acid may be used. In some embodiments, selenoglycoproteins are precipitated from the liquid phase comprising the extract of selenium enriched yeast soluble under the acidic conditions via raising the pH of the liquid phase. In some embodiments, the precipitated selenoglycoproteins are separated from the liquid phase via centrifugation to form a pellet of the precipitated selenoglycoproteins followed by removal of the liquid phase from the precipitated selenoglycoproteins. The invention is not limited by the amount or degree to which the pH of the extract is raised in order to precipitate the selenoglycoproteins from the liquid phase. In some embodiments, the pH of the liquid phase is raised to 1.85. In some embodiments, the pH of the liquid phase is raised to 3.0. In some embodiments, the pH of the liquid phase is raised to 4.0. In some embodiments, the pH of the liquid phase is raised to 6.0. In some embodiments, selenoglycoproteins are precipitated and separated from the liquid phase at a variety of pH conditions to generate multiple pH dependent fractions of soluble selenoglycoproteins. For example, in some embodiments, a single liquid phase comprising the extract of selenium enriched yeast soluble under acidic conditions is used to create a first fraction of soluble selenoglycoproteins precipitated at a first pH (e.g., pH of 1.85), a second fraction of soluble selenoglycoproteins precipitated at a second pH (e.g., pH of 3.0), a third fraction of soluble selenoglycoproteins precipitated at a third pH (e.g., pH of 4.0), and a fourth fraction of soluble selenoglycoproteins precipitated at a fourth pH (e.g., pH of 6.0). In some embodiments, precipitating the selenoglycoproteins from the liquid phase via raising the pH of the liquid phase comprises multiple, sequential pH dependent precipitation reactions of the liquid phase. In some embodiments, a composition comprising soluble selenoglycoproteins contains only a single, pH dependent fraction of the selenoglycoproteins (e.g., soluble selenoglycoproteins from liquid phase comprising the extract of selenium enriched yeast soluble under acidic conditions precipitated at pH 4.0). In some embodiments, a composition comprising soluble selenoglycoproteins contains two or more pH dependent fractions of selenoglycoproteins (e.g., soluble selenoglycoproteins from liquid phase comprising the extract of selenium enriched yeast soluble under acidic conditions precipitated at two or more different pH values).

In some embodiments, the selenium enriched yeast are dried, nonviable selenium-enriched yeast containing 2% or less inorganic selenium.

The invention also provides compositions comprising soluble selenoglycoproteins prepared according to the invention. For example, in some embodiments, the invention provides a selenium deficient composition comprising soluble selenoglycoproteins of the invention. In some embodiments, soluble selenoglycoproteins of the invention are added to and/or mixed with a selenium deficient composition. The invention is not limited by the type of selenium deficient composition or material to which soluble selenoglycoproteins of the invention are added to or mixed with, such compositions or materials including, but not limited to, dietary supplements, drugs, pharmaceuticals, foodstuffs, animal feeds, and other types of materials. In some embodiments, adding or mixing (e.g., admixing) selenoglycoprotein comprises admixing selenoglycoprotein and one or more other types of selenium into the composition. In some embodiments, soluble selenoglycoproteins of the invention are added to and/or mixed with compositions that contain selenium (e.g., to augment and/or supplement the total amount of selenium).

The invention also provides a composition comprising soluble selenoglycoproteins and a carrier. In some embodiments, the selenoglycoproteins are a specific pH dependent fraction of selenoglycoproteins. The invention is not limited by the type of carrier utilized. Indeed a variety of carriers may be used including, but not limited to, dendrimers, polymerosomes, nanoparticles, slow-release polymers, nanocapsules, and/or molecularly imprinted polymers. In one preferred embodiment, the carrier is a slow-release polymer. In another preferred embodiment, the carrier is a molecularly imprinted polymer. In still another preferred embodiment, the carrier is a polymersome used to encapsulate selenoglycoprotein. The invention is not limited by the type of polymersome used. Indeed, any polymersome known in the art may be utilized. In some embodiments, the polymersome comprises poly(ethylene oxide) (PEO) block copolymer. However, the invention is not so limited. Any known block copolymer may be utilized, including, for example poly(ethylethylene) (PEE), poly(butadiene) (PB or PBD), poly(styrene) (PS), and poly(isoprene) (PI). In some embodiments, the polymer comprises poly($\epsilon$-caprolactone) (PCL) diblock co-polymer. In some embodiments, the polymersome comprises poly(ethylene oxide)-block-poly($\epsilon$-caprolactone) (PEO-b-PCL) based diblock copolymers. In some embodiments, the polymersome comprises a block copolymer that is a triblock, tetrablock, pentablock, or at least six block copolymer. In some embodiments, the polymersome is derived from the coupling of poly(lactic acid), poly(glycolide), poly(lactic-coglycolic acid) and/or or poly(3-hydroxybutyrate) with PEO. The invention is not limited by the size of a polymersome encapsulated selenoglycoprotein. A variety of sizes find use in the compositions and methods of the invention including, but not limited to, polymersome encapsulated selenoglycoproteins that are about, 50-300 nm in diameter although larger (e.g., about 350 nm, 400 nm, 500 nm or larger) and smaller (e.g., about 40 nm, 30 nm, 20 nm, or smaller) polymersome encapsulated selenoglycoproteins may be used.

DEFINITIONS

Figure 1:
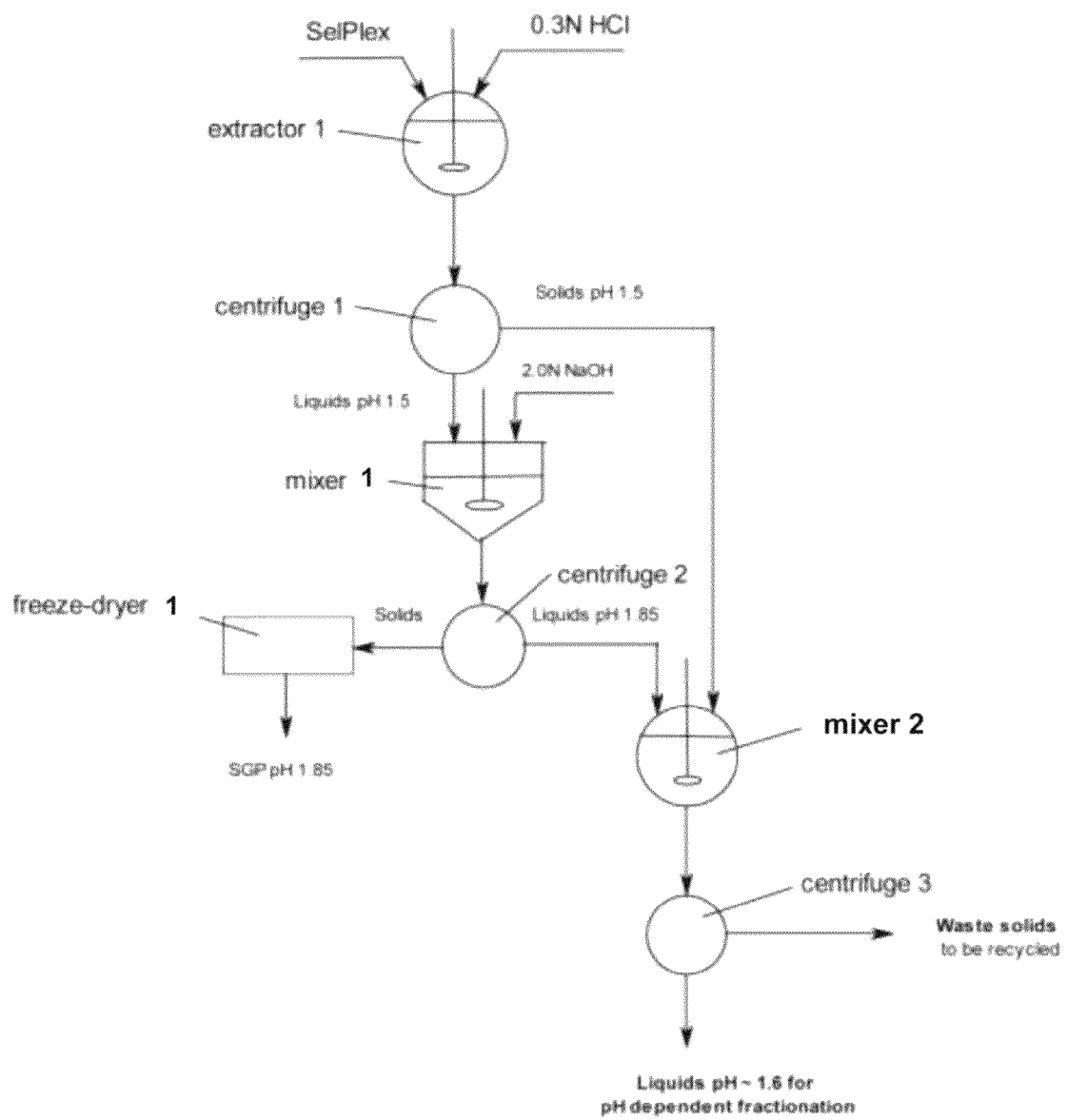
FIG. 1 shows sequential preparation of soluble selenoglycoproteins (SGPs) from SEL-PLEX by acidic extraction and subsequent precipitations of an embodiment of the invention.

To facilitate an understanding of the present invention, a number of terms and phrases are defined below:

As used herein, the terms "peptide," "polypeptide" and "protein" all refer to a primary sequence of amino acids that are joined by covalent "peptide linkages." In general, a peptide consists of a few amino acids, typically from 2-50 amino acids, and is shorter than a protein. The term "polypeptide" encompasses peptides and proteins.

The term "glycoprotein(s)" or "glycopeptides(s)" refers to a protein or peptide which contains one or more carbohydrate residues covalently attached to the polypeptide chain. The term "selenoprotein(s)" or "selenopeptide(s)" refers to a protein or peptide which contains one or more selenium atoms. Typically, selenium atoms are incorporated into proteins within selenium-containing amino acids including selenocysteine and selenomethionine.

The term "selenoglycoprotein(s)," "selenoglycopeptide(s)" or "SGP(s)" refers to a glycoprotein or glycopeptides which incorporate one or more selenium atoms. Typically, "selenoglycoproteins" comprise one or more selenium-containing amino acids. "Selenoglycoproteins" may comprise a number of carbohydrates in any number of different forms.

The terms "sample" and "specimen" are used in their broadest sense and encompass samples or specimens obtained from any source. As used herein, the term "sample" is used to refer to biological samples obtained from animals (including humans), and encompasses fluids, solids and tissues. In some embodiments of this invention, biological samples include cerebrospinal fluid (CSF), serous fluid, urine and saliva, blood, and blood products such as plasma, serum and the like. However, these examples are not to be construed as limiting the types of samples that find use with the present invention.

As used herein, the term "yeast" and "yeast cells" refers to eukaryotic microorganisms classified in the kingdom Fungi, having a cell wall, cell membrane and intracellular components. Yeasts do not form a specific taxonomic or phylogenetic grouping. Currently about 1,500 species are known; it is estimated that only 1% of all yeast species have been described. The term "yeast" is often taken as a synonym for S. cerevisiae, but the phylogenetic diversity of yeasts is shown by their placement in both divisions Ascomycota and Basidiomycota. The term "yeast" encompasses brewer's yeast, distillers yeast and Baker's yeasts. The budding yeasts ("true yeasts") are classified in the order Saccharomycetales. Most species of yeast reproduce asexually by budding, although some reproduce by binary fission. Yeasts are unicellular, although some species become multicellular through the formation of a string of connected budding cells known as pseudohyphae, or false hyphae. Yeast size can vary greatly depending on the species, typically measuring 3-4 µm in diameter, although some yeast can reach over 40 µm.

As used herein, the terms "selenium-enriched yeast" and "selenized yeast" refer to any yeast (e.g., Saccharomyces cerevisiae) that is cultivated in a medium containing inorganic selenium salts. The present invention is not limited by the selenium salt used. Indeed, a variety of selenium salts are contemplated to be useful in the present invention including, but not limited to, sodium selenite, or sodium selenate. Free selenomethionine (e.g., not associated with a cell or yeast) can also be used as the selenium source for selenium enriched yeast as yeast does incorporate this form of selenium. During cultivation, because of the chemical similarity between selenium and sulfur, yeast incorporate selenium in place of sulfur in what are normally sulfur-containing organic compounds within the cell. A selenium-containing compound in such yeast preparations is selenomethionine that is incorporated into polypeptides/proteins. The amount of total cellular selenium present in the form of selenomethionine in such preparations will vary, but can be between 10 and 100%, 20-60%, 50-75% and between 60 and 75%. The remainder of the organic selenium in selenized yeast preparations is predominantly made up of intermediates in the pathway for selenomethionine biosynthesis. These include, but are not limited to, selenocysteine, selenocystathionine, selenohomocysteine and seleno-adenosylselenomethionine. The amount of residual inorganic selenium salt in the finished product is generally quite low (e.g., <2%).

As used herein, the term "SEL-PLEX" refers to a dried, nonviable selenium-enriched yeast (e.g. Saccharomyces cerevisiae of accession number CNCM I-3060, Collection Nationale De Cultures De Microorganismes (CNCM), Institut Pasteur, Paris, France) cultivated in a fed-batch fermentation that provides incremental amounts of cane molasses and selenium salts in a manner that minimizes the detrimental effects of selenium salts on the growth rate of the yeast and allows for optimal incorporation of inorganic selenium into cellular organic material. Residual inorganic selenium is eliminated (e.g., using a rigorous washing process) and does not exceed 2% of the total selenium content.

As used herein, the term "organic selenium" refers to any organic compound wherein selenium atom is directly connected to a carbon atom.

As used herein, the term "inorganic selenium" generally refers to any selenium salt (e.g., sodium selenite, sodium selenate) in which selenium is at −2, +4 and +6 oxidation state.

As used herein, the terms "host," "subject" and "patient" refer to any animal, including but not limited to, humans and animals (e.g., primates, dogs, cats, cows, horses, sheep, poultry, fish, crustaceans, etc.) that is studied, analyzed, tested, diagnosed or treated. As used herein, the terms "host," "subject" and "patient" are used interchangeably, unless indicated otherwise.

As used herein, the term "w/w" ("weight/weight") refers to the amount of a given substance in a composition on weight basis. For example, an animal feed comprising 0.02% w/w dietary feed supplement means that the mass of the dietary feed supplement is 0.02% of the total mass of the animal feed (e.g., 200 grams of dietary feed supplement composition in 999,800 grams of animal feed).

As used herein, the term "purified" or "to purify" refers to the removal of components from a sample. For example, yeast cell walls are purified by removal of non-yeast cell wall components (e.g., plasma membrane and/or yeast intracellular components); they are also purified by the removal of contaminants or other agents other than yeast cell wall. The removal of non-yeast cell wall components and/or non-yeast cell wall contaminants results in an increase in the percent of yeast cell wall or components thereof in a sample.

As used herein, the term "effective amount" refers to the amount of a composition (e.g., comprising selenoglycoproteins of the present invention sufficient to effect beneficial or desired results. An effective amount can be administered in one or more administrations, applications or dosages and is not intended to be limited to a particular formulation or administration route.

As used herein, the term "bioavailability" refers to the fraction of a molecule or component that is available to an organism or reaches the systemic circulation. When a molecule or component is administered intravenously, its bioavailability is quite high. However, when a molecule or component is administered via other routes (such as orally), its bioavailability decreases (due to incomplete absorption and first-pass metabolism). In a nutritional setting, bioavailability refers to the rates of absorption and utilization of a nutrient. Different forms of the same nutrient, for example, may have different bioavailabilities.

As used herein, the terms "feed", "foodstuffs", "animal feed", and "feedstuffs" refer to material(s) that are consumed by animals and contribute energy and/or nutrients to an animal's diet. Examples include, but are not limited to, Total Mixed Ration (TMR), forage(s), pellet(s), concentrate(s), premix(es) coproduct(s), grain(s), distiller grain(s), molasses, fiber(s), fodder(s), grass(es), hay, kernel(s), leaves, meal, soluble(s), and supplement(s).

As used herein, the terms "food supplement," "dietary supplement," "dietary supplement composition," and the like refer to a food product formulated as a dietary or nutritional supplement to be used as part of a human or animal diet, e.g. as an addition to animal feed.

As used herein, the terms "administration" and "administering" refer to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., composition comprising selenoglycoproteins of the invention and one or more other agents—e.g., an antibiotic, a therapeutic (e.g., drug or pharmaceutical), or, other biologically active compound) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" or grammatical equivalents encompasses the improvement and/or reversal of the symptoms of disease (e.g., neurodegenerative disease). A compound which causes an improvement in any parameter associated with disease when used in the screening methods of the instant invention may thereby be identified as a therapeutic compound. The term "treatment" refers to both therapeutic treatment and prophylactic or preventative measures. For example, those who may benefit from treatment with compositions and methods of the present invention include those already with a disease and/or disorder (e.g., neurodegenerative disease, diabetes or lack of or loss of cognitive function) as well as those in which a disease and/or disorder is to be prevented (e.g., using a prophylactic treatment of the present invention).

As used herein, the term "at risk for disease" refers to a subject (e.g., a human) that is predisposed to experiencing a particular disease. This predisposition may be genetic (e.g., a particular genetic tendency to experience the disease, such as heritable disorders), or due to other factors (e.g., age, weight, environmental conditions, exposures to detrimental compounds present in the environment, etc.). Thus, it is not intended that the present invention be limited to any particular risk, nor is it intended that the present invention be limited to any particular disease.

As used herein, the term "suffering from disease" refers to a subject (e.g., a human) that is experiencing a particular disease. It is not intended that the present invention be limited to any particular signs or symptoms, nor disease. Thus, it is intended that the present invention encompass subjects that are experiencing any range of disease (e.g., from sub-clinical manifestation to full-blown disease) wherein the subject exhibits at least some of the indicia (e.g., signs and symptoms) associated with the particular disease.

As used herein, the terms "disease" and "pathological condition" are used interchangeably to describe a state, signs, and/or symptoms that are associated with any impairment of the normal state of a living animal or of any of its organs or tissues that interrupts or modifies the performance of normal functions, and may be a response to environmental factors (such as radiation, malnutrition, industrial hazards, or climate), to specific infective agents (such as worms, bacteria, or viruses), to inherent defect of the organism (such as various genetic anomalies), or to combinations of these and other factors.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of disease (e.g., cancer, neurodegenerative disease, etc.).

As used herein, the term "kit" is used in reference to a combination of reagents and other materials. It is contemplated that the kit may include reagents such as nutrients and drugs as well as administration means. It is not intended that the term "kit" be limited to a particular combination of reagents and/or other materials.

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., composition comprising selenoglycoproteins) with a carrier, inert or active, making the composition especially suitable for diagnostic, preventative and/or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells that line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. Examples of carriers, stabilizers and adjuvants are described, for example, in Martin, Remington's Pharmaceutical Sciences, 15th Ed., Mack Publ. Co., Easton, Pa. (1975), incorporated herein by reference). In some embodiments, a foodstuff (e.g., dietary material and/or treatment) acts as a carrier (e.g., of a selenoglycoprotein composition of the invention).

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts. Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like. Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "drying" refers to spray drying, freeze drying, air drying, vacuum drying or any other kind of process that reduces or eliminates liquid in a substance.

As used herein, the term "spray drying" refers to a commonly used method of drying a substance containing liquid using hot gas to evaporate the liquid to reduce or eliminate liquid in the substance. In other words the material is dried by way of spraying or atomizing into a draft of heated dry air.

As used herein, the term "freeze-drying" and the term "lyophilization" and the term "cryodesiccation" refer to the removal of a solvent from matter in a frozen state by sublimation. This is accomplished by freezing the material to be dried below its eutectic point and then providing the latent heat of sublimation. Precise control of vacuum and heat input permits drying from the frozen state without product meltback. In practical application, the process is accelerated and precisely controlled under reduced pressure conditions.

As used herein, the term "dry free flowing powder" refers to a free flowing dry powder, e.g. a powder that can be poured from a container, bag, vessel etc without hindrance of large clumps.

As used herein, the term "grinding" refers to reducing particle size by impact, shearing, or attrition.

As used herein, the term "washing" refers to the removal or cleansing (e.g., using any type of solute (e.g. distilled water, buffer, or solvent) or mixture) of impurities or soluble unwanted component of a preparation (e.g., a yeast cell wall) may be washed to remove non-yeast cell wall components from the sample).

As used herein, the term "polymersome" refers to vesicles that are assembled from synthetic polymers in aqueous solution (e.g., that can be utilized to encapsulate a material). Polymersomes can be made using amphiphilic synthetic block copolymers to form the vesicle membrane, and have radii ranging from 50 nm to 5 μm or more. Most polymersomes contain an aqueous solution in their core and are useful for encapsulating and protecting sensitive molecules, such as drugs, enzymes, other proteins and peptides as well as DNA and RNA fragments. The polymersome membrane provides a physical barrier that isolates the encapsulated material from external materials, such as those found in biological systems. Examples of polymersomes that find use in embodiments of the invention, as well as their synthesis, can be found, for example, in U.S. Pat. Nos. 7,867,512, 7,682,603, and 6,835,394, each of which is hereby incorporated by reference in its entirety.

As used herein, the term "waste" refers to unwanted or useless materials.

As used herein, the term "wastewater" is any water that has been adversely affected in quality by anthropogenic influence.

DETAILED DESCRIPTION OF THE INVENTION

I. Introduction

Selenium is a trace element involved in regulating aspects of the antioxidant defense mechanism in all living tissues by interacting with the body's glutathione (GSH) and its major Se-containing antioxidant enzymes, glutathione peroxidase (GPX) and thioredoxin reductase (See, e.g., Goehring et al., J. Anim. Sci. 59, 725-732 (1984); Gerloff et al., J. Anim. Sci. 70, 3934-3940 (1992); herein incorporated by reference in their entireties). Glutathione and GPX have the capacity to protect the integrity of unsaturated bonds of membrane phospholipids by extinguishing free radical attacks capable of initiating and propagating lipid oxidation (See, e.g., Meister and Anderson, Annu Rev. Biochem. 52, 711-760 (1983); Deleve and Kaplowitz, Pharm. Ther. 52, 287-305 (1991); Palmer and Paulson, Nutr. Rev. 55, 353-361 (1997); herein incorporated by reference in their entireties).

Selenium has also been associated with reduced cancer risk in several epidemiologic studies (See, e.g., Salonen et al., Am. J. Epidemiol. 120: 342-349 (1984); Willett et al., Lancet 2: 130-134 (1983); Virtamo et al., Cancer 60: 145-148 (1987); herein incorporated by reference in their entireties). Various selenium compounds of natural and synthetic origin have been shown to inhibit tumor development in animal studies in a wide range of dosages (See, e.g., Ip, J. Nutr. 128: 1845-1854 (1998); herein incorporated by reference in its entirety). Although most animal studies have employed pharmacologic doses of selenium (>2 mg/kg) in cancer chemoprevention (See, e.g., Ip, J. Nutr. 128: 1845-1854 (1998)), selenium deficiency has also been shown to enhance mammary (See, e.g., Ip and Daniel, Cancer Res. 45: 61-65 (1985); herein incorporated by reference in its entirety) and UVB-induced skin carcinogenesis (See, e.g., Pence et al., 102: 759-761 (1994); herein incorporated by reference in its entirety).

Yeast cell wall proteins are connected to cell wall polysaccharides by chemical bond, and in order to release yeast cell wall protein into solution, these bonds need to be broken. The standard practice for protein extraction from yeast cell wall is to break the bonds using alkaline hydrolysis (pH 11.5, 80° C.) before centrifuging to separate proteins from glucan polysaccharides that are insoluble in water.

Experiments conducted during development of embodiments of the invention were performed in an attempt to extract selenoglycoproteins using the standard practice of alkaline hydrolysis. These attempts to extract selenoglycoproteins from yeast cell wall using alkaline hydrolysis failed. It was later learned that the failure to extract selenoglycoproteins from yeast cell wall using alkaline hydrolysis was due to destruction of the selenoglycoproteins. Later attempts to extract selenoglycoproteins were conducted using a modified alkaline hydrolysis procedure (pH 11.5, 60° C.). These attempts also failed to extract selenoglycoproteins from yeast cell wall. The typical, alkaline, yeast protein extraction methods did not work when attempting to extract selenoglycoproteins from yeast. Thus, additional experiments were conducted during development of embodiments of the invention that attempted to extract selenoglycoproteins using an acidic extraction (pH 5, 80° C.). As described herein, the acidic extraction method was successful; the selenoglycoproteins were not destroyed and extraction was possible.

Thus, in some embodiments, the invention provides novel methods for obtaining selenoglycoproteins (SGPs), selenoglycoprotein (SGP) compositions (e.g., obtained using acidic extraction methods (e.g., pH dependent selenoglycoprotein fractions), compositions comprising encapsulated selenoglycoproteins (SGP's), and methods of using the same (e.g., to provide in vivo benefit (e.g., changes in gene expression profiles) to a subject (e.g. human, animal, etc.)). In particular, experiments conducted during development of embodiments of the invention demonstrate that compositions (e.g., comprising SGP (e.g., isolated via a method of the invention)) and methods of the invention can be used to provide biologically available selenium to a subject (e.g., thereby increasing the selenium content of tissue and/or muscle within the subject (e.g., thereby leading to a stabilization and/or increase of the health of a subject))). In some embodiments, the invention provides methods for obtaining SGP's, compositions comprising encapsulated (e.g., polymersome encapsulated) SGP's and methods of using the same to alter cellular function (e.g., thereby providing beneficial effects to a system of a subject (e.g., including, but not limited to, musculoskeletal system, the neurological system, the nervous system, the endocrine system, the metabolic system, and/or the immune system). The invention also provides methods of using SGPs alone or in combination with one or more other active agents for treating or preventing disease (e.g., cancer growth and/or metastasis). The invention also provides methods of using SGPs to enhance animal (e.g. livestock) health. In some embodiments, compositions of the invention are utilized to supplement, improve and/or enhance the health and/or nutritional value of food products (e.g. meat, dairy, eggs, etc.). In some embodiments, the invention provides compositions comprising SGPs and methods of using the same as a therapeutic, nutritional supplement, and/or prophylactic treatment (e.g., for general health, for boosting the immune system, for neurodegenerative disease, for enhancing cognitive function, for the treatment or prevention of cancer, tumor growth and/or metastasis, etc.), and methods of making, producing, purifying, isolating, extracting, and/or characterizing the same. The invention also provides SGPs and methods of using SGPs for feeding animals and/or supplementing animal feed.

The invention also provides soluble selenium compositions (e.g. SGPs) and methods of use, production, and purification thereof. For example, in some embodiments, the invention provides soluble SGPs (See, e.g., Examples 1-2 describing the generation of (e.g., separation and characterization of) pH dependent SGP fractions), and compositions and methods for administration thereof (See, e.g., Examples 3-4). In some embodiments, the invention provides selenium (e.g. organic selenium (e.g., pH dependent SGP fraction of SEL-PLEX or other selenium enriched yeast)) in a soluble form which is administered to a subject through a variety of routes (e.g. oral, topical, intravenous, etc.). In some embodiments, the invention provides a low-fiber soluble selenium (e.g. organic selenium) composition. In some embodiments, the invention provides compositions and methods for soluble organic selenium delivery systems (e.g. polymersome encapsulated selenoglycoproteins, nanocapsules, polymers, etc.).

Yeast (e.g. *Saccharomyces cerevisiae*), grown in medium containing selenium (e.g. inorganic selenium (e.g. sodium selenite ($Na_2SeO_3$))) metabolize the selenium (e.g. inorganic selenium) and incorporate selenium instead of sulfur into cysteine and methionine, yielding proteins containing selenoaminoacids (SeCys and SeMet) (Demirci et al. J. Agric. Food Chem. 47, 2496-2500 (1999)., Demirci & Pometto. J. Agric. Food Chem. 47, 2491-2495 (1999), Ouerdane & Mester. J. Agric. Food Chem. 56,11792-11799, (2008), each of which is herein incorporated by reference in their entireties). ALLTECH, Inc. (Nicholsville, Ky., USA) produces spray-dried selenium enriched yeast sold under the name of SEL-PLEX as a feed and food nutritional supplement, containing "organic selenium" (See, e.g., Korhola et al. Res. 18, 65-68, (1986)., herein incorporated by reference in its entirety). The minimum concentration of selenium in SEL-PLEX is 1500 ppm and proteins are the exclusive carriers of it (See, e.g., Surai. Nottingham University Press 2002, 234-236 (2002), Kelly & Power. J. Dairy Sci. 78, 237-242 (1995), McSheehy et al. Analyst 130, 35-37 (2005), herein incorporated by reference in their entireties). There are two pools of proteins in yeast: proteins present inside of the yeast cell and proteins associated with the yeast cell wall mannan (See, e.g., Sedmak. US Patent Appl. Publication Pub. No.: US 2006/0263415., herein incorporated by reference in its entirety). About 17.0 weight % of commercial SEL-PLEX is soluble in water, and this material contains less than 6.5% of total selenium that is present in SEL-PLEX. Chicken feeding studies in which SEL-PLEX and sodium selenite were used as the sources of selenium, indicated much better selenium transfer into a chicken breast muscle by SEL-PLEX. A variety of bio-activities were discovered for oral administration of SEL-PLEX (See, e.g., Rayman. The Lancet 356, 233-241 (2000), McKenzie Trends in Immunology 19, 342-345 (1998), Tapiero. Biomedicine & Pharmacotherapy 57, 134-144 (2003), Combs & Grey Pharmacol. Ther. 79, 179-192 (1998), Clark et. al. J. Am. Med. Assoc. 276, 1957-1963 (1996), herein incorporated by reference in their entireties).

In some embodiments, the invention provides separation, and physical and chemical characterization of soluble selenoglycoproteins (SGP's) from yeast (e.g. *Saccharomyces cerevisiae*) grown in medium containing selenium (e.g. inorganic selenium (e.g. sodium selenite)), and their active participation in "organic selenium" delivery to tissues (e.g. human, animal, chicken, etc.), by feeding the subject food (e.g. feed) supplemented with or otherwise containing SGP's of the invention (See, e.g. Examples 1-4). The invention provides tissue-targeted, intravenous, oral, and/or trans-dermal delivery of active, soluble selenium components (e.g., pH dependent SGP fractions of a selenium, enriched yeast (e.g., SEL-PLEX)). In some embodiments, the invention provides slow-release forms of "organic selenium" delivery systems (e.g. nanocapsules, polymer spheres, and polymersome encapsulated SGPs) (See, e.g. Examples 5-9). In some embodiments, the invention provides a composition comprising polymersome encapsulated SGP's. In some embodiments the invention provides enhanced delivery and improved biodistribution of SGP's by encapsulating SGP's inside poly (ethylene oxide)-block-poly(ε-caprolactone) (PEO-b-PCL) based polymersomes.

Separation of various yeast cell components by extracting cell wall from intracellular components of yeast cells has been described (See, e.g., Otero et al. J. Chem. Tech. Biotechnol. 66, 67-71 (1996), herein incorporated by reference in its entirety). These separation techniques have not been applied to the extraction of spray-dried selenium yeast. The conventional, alkaline conditions (pH 9.0-14.0) used in the art in extraction of glycoproteins from yeast (See, e.g., Roberge et. al. J. Agric. Food Chem. 51, 4191-4197 (2003), herein incorporated by reference in its entirety) failed because SeH or SeMe substituents were eliminated from selenocystine or selenomethionine amino acids. In other words, the desired substituents decomposed and as a result selenium that was present in the original SGP's was lost during attempted extraction in alkaline conditions when applied to extraction of yeast containing selenoproteins (See, e.g., Table 12 of Example 8).

Accordingly, in some embodiments, the invention provides selenoglycoprotein compositions (e.g., comprising a pH dependent fraction of selenoglycoproteins described herein) and methods of utilizing the same. In some embodiments, the invention provides methods of producing, purifying, isolating, extracting, separating, precipitating, and/or characterizing selenoglycoproteins (e.g. from selenium enriched yeast). In some embodiments, the invention provides compositions and methods for the delivery of soluble selenium compositions (e.g. SGPs (e.g., pH dependent SGP fractions)) to a subject, including dietary supplement compositions (e.g. comprising SGPs (e.g., pharmaceuticals, nutriceuticals, supplements, foodstuffs, etc)). In some embodiments, the invention provides compositions and methods for advanced delivery (e.g. directed delivery, time-release delivery, etc.) of selenium (e.g. SGPs (e.g., polymersomes, nanocapsules, nanoparticles, polymers, etc.)). Compositions and methods of the invention find use in a variety of applications including but not limited to dietary (e.g., admixing with feedstuffs or otherwise feeding to animals), preventative, therapeutic as well as research applications. Accordingly, in some embodiments, the invention provides animal feed compositions (e.g. comprising SGPs (e.g. soluble SGPs (e.g. soluble organic selenium))), methods of manufacturing the compositions and methods of providing nutrition (e.g. comprising SGPs (e.g. soluble SGPs (e.g. soluble organic selenium))) to animals comprising providing the compositions to the animals.

II. Extraction, Separation, Purification and Use

In some embodiments of the invention, soluble selenium is obtained in the form of selenoglycoproteins (SGPs). In some embodiments, SGPs are extracted from a general source of selenoproteins (e.g. selenium enriched yeast (e.g. SEL-PLEX)). In some embodiments, extraction and/or purification of SGPs comprises one or more pH-dependant extraction/precipitation steps (e.g., as described in Examples 1 and 2). In some embodiments, extraction and/or purification of SGPs comprises one or more pH-dependant fractionation steps. In some embodiments the invention provides acidic extraction of selenium enriched yeast (e.g. SEL-PLEX) to solubilize SGP's (e.g., without denaturing and/or destroying the SGPs). In some embodiments, the invention provides that pH-dependent precipitation of SGPs from an acidic extract (e.g., as described in Examples 1-2) produces increased content of selenoglycoproteins, decreased content of non-digestible fibers, and a high concentration of selenium (e.g., a concentration of selenium that is higher than that present in SEL-PLEX). Thus, in some embodiments, the invention provides SGP extracted from selenium enriched yeast wherein the selenium content of the SGP is greater than the selenium content of the material from which the SGP was extracted (e.g., in wt/wt %, ppm, etc.). In some embodiments, the invention provides selenium in the form of a pH dependent SGP fraction (e.g., pH 4.0 or pH 6.0 fractions) of selenium enriched yeast (e.g., SEL-PLEX) that displays the same or highly similar level of bioavailability when administered to a subject compared to the bioavailability of selenium from the selenium enriched yeast (e.g., SEL-PLEX) parent source (See, e.g., Example 3, Table 5).

In some embodiments, SGPs are extracted from a general source of selenoproteins (e.g. selenium enriched yeast cells (e.g. SEL-PLEX)). In some embodiments, a portion of the selenoproteins in a selenoprotein source comprises SGPs (e.g. 0.1% . . . 0.2% . . . 0.5% . . . 1.0% . . . 2.0% . . . 5.0% . . . 10% . . . 20% . . . 50% or more SGPs). In some embodiments, a selenoprotein source comprises cells (e.g. yeast cells) which have been grown in the presence of Se-containing media (e.g. Se-rich media). In some embodiments, Se-containing cells (e.g. yeast cells) are processed to extract, isolate, and/or purify selenoproteins resulting in a selenoprotein source or selenoprotein-rich composition (e.g. SGP-rich composition). In some embodiments, a sample comprising selenoproteins and SGPs is enriched for SGPs.

In some embodiments, a selenoprotein source or selenoprotein-rich composition (e.g. selenium-enriched yeast source (e.g. SEL-PLEX)) is subjected to one or more steps to yield isolated, purified, separated, and/or extracted SGPs. In some embodiments, a selenoprotein source is mixed (e.g. in a liquid carrier (e.g. water, buffer, salt, etc.)) to produce a protein slurry, mixture, lysate, and/or solution. In some embodiments, the selenoprotein source (e.g. selenium-enriched yeast source (e.g. SEL-PLEX)) is mixed at high temperature (e.g. above freezing, above room temperature, 30° C. . . . . 40° C. . . . . 50° C. . . . . 60° C. . . . . 70° C. . . . . 80° C. . . . . 90° C. or higher). In some embodiments, the selenoprotein source (e.g., selenium-enriched yeast source (e.g. SEL-PLEX)) is mixed at low pH (e.g. acidic conditions (e.g. pH about 0.5, about 1.0, about 1.5, about 2.0, about 3.0, about 4.0, about 4.5, about 5.0, about 5.5, about 6.0 or about 6.5). In some embodiments, the selenoprotein source (e.g. selenium-enriched yeast source (e.g. SEL-PLEX)) is gently mixed, rapidly mixed, thoroughly mixed, vigorously mixed, etc. In some embodiments, the selenoprotein source (e.g., selenium-enriched yeast source (e.g. SEL-PLEX)) is mixed at low pH (e.g. acidic conditions (e.g. pH about 0.5, about 1.0, about 1.5, about 2.0, about 3.0, about 4.0, about 4.5, about 5.0, about 5.5, about 6.0 or about 6.5) and high temperature (e.g. above freezing, above room temperature, 30° C. . . . . 40° C. . . . . 50° C. . . . . 60° C. . . . . 70° C. . . . . 80° C. . . . . 90° C., or higher)). In some embodiments, the pH of the mixture is maintained through the addition of acid or base.

In some embodiments, the selenoprotein-containing mixture is centrifuged to separate the liquid/soluble and solid/insoluble phases. In some embodiments, a centrifuge speed is selected that is sufficient to separate the phases. In some embodiments, the liquid phase comprises soluble SGPs. In some embodiments, the pH of the liquid phase is adjusted (e.g. raised) to precipitate a portion of the SGPs. In some embodiments, the pH of the liquid fraction is raised slightly to moderately (e.g., pH raised by about 0.1 . . . 0.2 . . . 0.5 . . . 1.0 . . . 2.0) to precipitate SGPs which were soluble at the original pH, but not the elevated pH. In some embodiments, the pH of the liquid fraction is raised significantly (e.g., pH raised by about 1.0 . . . 2.0 . . . 3.0 . . . 4.0 . . . 5.0 . . . 6.0) to precipitate a large portion of the SGPs which were soluble at the original pH. In some embodiments, selenoglycoproteins are precipitated and separated from the liquid phase at a variety of pH conditions to generate multiple pH dependent fractions of soluble selenoglycoproteins. For example, in some embodiments, a single liquid phase comprising the extract of selenium enriched yeast soluble under acidic conditions is used to create a first fraction of soluble selenoglycoproteins precipitated at a first pH (e.g., pH of 1.85), a second fraction of soluble selenoglycoproteins precipitated at a second pH (e.g., pH of 3.0), a third fraction of soluble selenoglycoproteins precipitated at a third pH (e.g., pH of 4.0), and a fourth fraction of soluble selenoglycoproteins precipitated at a fourth pH (e.g., pH of 6.0). In some embodiments, precipitating the selenoglycoproteins from the liquid phase via raising the pH of the liquid phase comprises multiple, sequential pH dependent precipitation reactions of the liquid phase.

In some embodiments, precipitated SGPs are separated from the pH-adjusted liquid fraction by centrifugation (e.g. at sufficient speed to produce separate liquid and solid phases). In some embodiments, SGPs that have been separated from the liquid phase are freeze dried to yield a solid SGP fraction.

In some embodiments, the process of raising the pH of the liquid phase and centrifuging to isolate the SGP fraction is repeated to produce SGP fractions of different solubility (e.g. soluble below pH 1.5 . . . soluble below pH 2 . . . soluble below pH 3 . . . soluble below pH 4 . . . soluble below pH 5 . . . soluble below pH 6, etc.). In some embodiments, a single pH adjustment and centrifugation steps are performed to produce one fraction containing SGPs of a desired solubility (e.g. soluble below pH 1.5 . . . soluble below pH 2 . . . soluble below pH 3 . . . soluble below pH 4 . . . soluble below pH 5 . . . soluble below pH 6, etc.). In some embodiments, the liquid phase that remains after removal of the final SGP fraction finds utility as a component of growth media for cells used in further production of selenoproteins or SGPs. In some embodiments, a composition comprising soluble selenoglycoproteins contains only a single, pH dependent fraction of the selenoglycoproteins (e.g., soluble selenoglycoproteins from liquid phase comprising the extract of selenium enriched yeast soluble under acidic conditions precipitated at pH 4.0). In some embodiments, a composition comprising soluble selenoglycoproteins contains two or more pH dependent fractions of selenoglycoproteins (e.g., soluble selenoglycoproteins from liquid phase comprising the extract of selenium enriched yeast soluble under acidic conditions precipitated at two or more different pH values).

Figure 2:
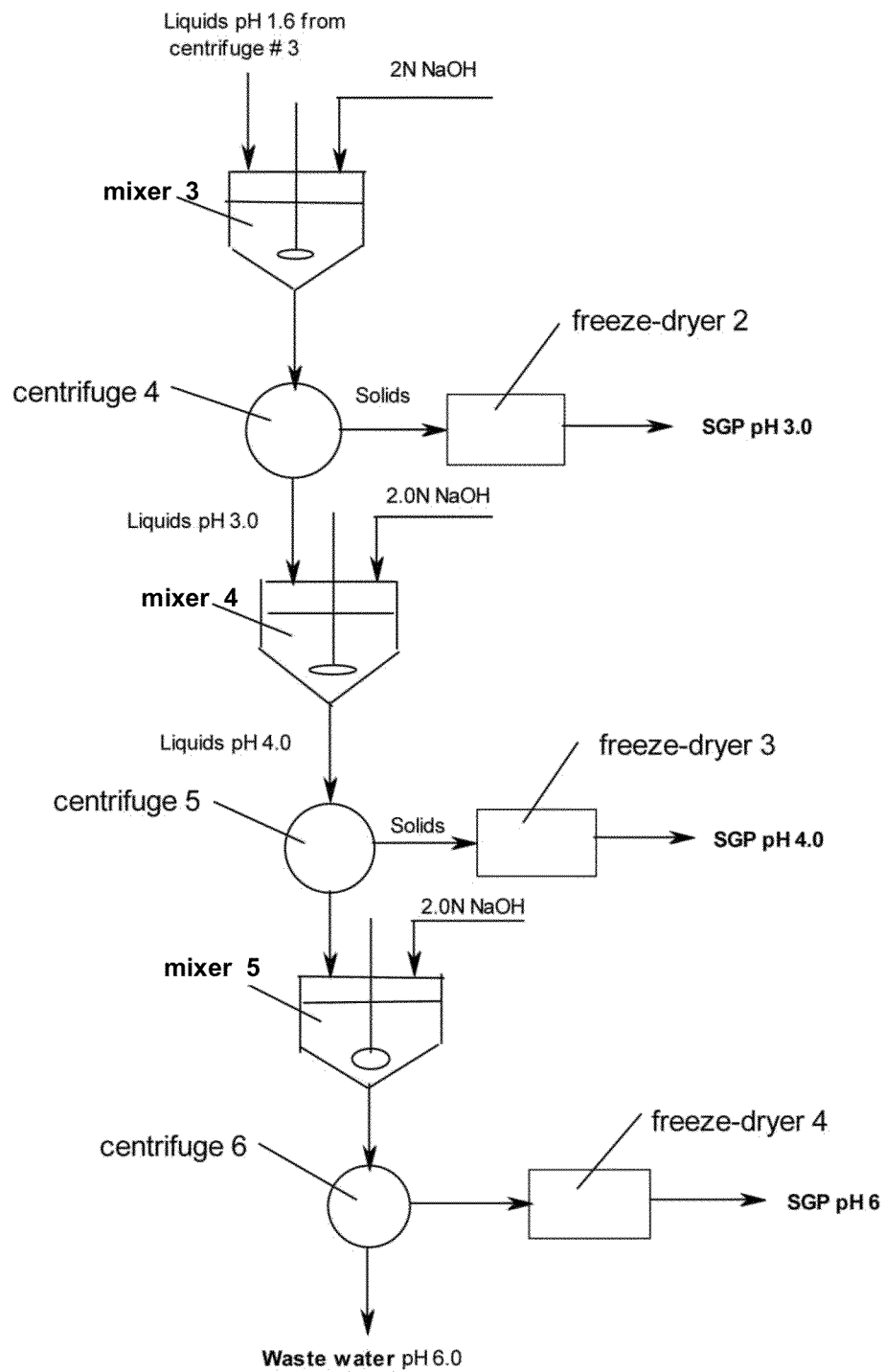
FIG. 2 shows a process of pH dependent precipitation of selenoglycoproteins of an embodiment of the invention.
Figure 3:
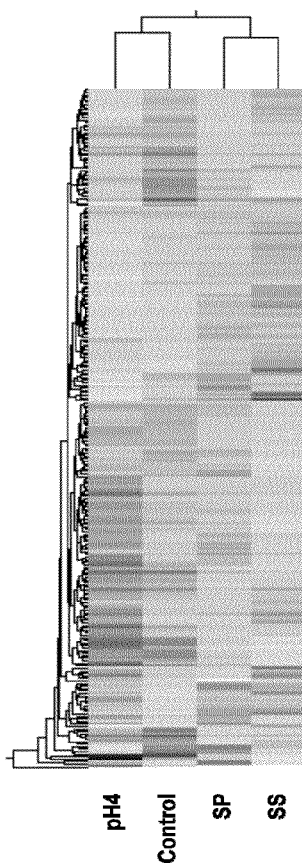
FIG. 3 shows a heat map representing the effects of different selenium-supplemented treatments described in Tables 3 and 4 of Example 3 on gene expression levels in chicken breast skeletal muscle relative to a basal control.

In a preferred embodiment, the process of SGP extraction from a selenoprotein source (e.g. selenium enriched yeast (e.g., SEL-PLEX)) and pH dependent fractionation of the mixture of SGP's (See, e.g., FIGS. 2 and 3) comprises two stages (See e.g., Examples 1-2, FIGS. 1 and 2). In the first stage, a suspension of selenium enriched yeast in 0.3N HCl (pH 1.5) is stirred and heated at 80° C. for 8 hrs. The pH of the mixture is maintained at pH1.5 by adding concentrated HCl during the first hour of the extraction. After eight hours, the mixture is centrifuged, and the liquid phase is separated. The pH of the solution is adjusted to 1.85, by the addition of 2.0N NaOH and SGP's that have limited solubility at this pH precipitate from the solution and are separated from the liquids (pH 1.85) by the second centrifugation and then freeze-dried to yield solid SGP fraction of pH 1.85. In some embodiments, the liquids (pH 1.85) are mixed with the solids (pH 1.5) from the first centrifugation, which results in change of the pH of the mixture to pH 1.6. The majority of the SGP's soluble at pH 1.6, are transferred into the liquid phase, without increasing the volumes of the waste streams created within this stage of the process. The major by-product from this stage of the process are solids from the second centrifugation. The stream of waste solids constitutes about 56.5 weight % of the selenium enriched yeast taken for extraction and contains valuable selenium yeast cell wall material containing 38.91% of protein and 2477 ppm of selenium. In some embodiments, these solids are utilized (e.g., alone or in combination with other material (e.g., selenium enriched yeast)) as an environmentally friendly nutritional supplement in animal diets. In the second stage (See, e.g., FIG. 3), the liquid phase (pH 1.6) from the second centrifugation (SEE FIG. 2) is transferred to a mixer and the pH is adjusted to pH 3.0 by the addition of 2.0N NaOH and SGP's that have limited solubility at this pH precipitate from the solution and are separated from the liquids (pH 3.0) by the third centrifugation and finally freeze-dried to yield solid SGP fraction of pH 3.0 (See, e.g., Examples 1-2 and FIGS. 2 and 3). The liquid phase (pH 3.0) from the third centrifugation is transferred to a mixer and the pH adjusted to pH 4.0 by the addition of 2.0N NaOH and SGP's that have limited solubility at this pH precipitate from the solution and are separated from the liquids (pH 4.0) by the fourth centrifugation and finally freeze-dried to yield solid SGP fraction of pH 4.0. The liquid phase (pH 4.0) from the fourth centrifugation is transferred to a mixer and the pH is adjusted to pH 6.0 by the addition of 2.0N NaOH and SGP's that have limited solubility at this pH precipitate from the solution and are separated from the liquids (pH 6.0) by the fifth centrifugation and then freeze-dried to yield solid SGP fraction of pH 6.0. The only waste stream produced at the second stage of the process is the waste water stream, containing 13.4 weight % of solids (in comparison with the weight of selenium enriched yeast used in extraction) out of which the protein fraction constitutes about 13.3 weight %, sodium chloride for 3.6 weight % and glucose and mannose mono- and oligosaccharides constitute above 80 weight %. This "waste water" stream of pH 6.0 and selenium concentration of 242 ppm can be recycled or otherwise reused to the preparation of a new batch of selenium yeast (e.g. utilized in growth media).

In some embodiments, SGP's precipitated at pH 4.0 exhibit superior selenium delivery (e.g. to muscle tissue) as compared to selenium enriched yeast (e.g. SEL-PLEX) and far superior delivery when compared to inorganic forms of selenium (e.g. sodium selenite) (See, e.g. Example 3). Additionally, pH dependent selenoglycoprotein fractions (e.g., pH 6.0) are different compositionally than selenium enriched yeast (e.g., SEL-PLEX) and allow for delivery of similar amounts of selenium while requiring much less of the starting material (e.g., selenium enriched yeast).

In some embodiments, a SGP extraction procedure comprises 4 or fewer of the pH adjustment and centrifugation steps of the above procedure (e.g. 1 pH adjustment and centrifugation step, 2 pH adjustment and centrifugation steps, 3 pH adjustment and centrifugation steps, 4 pH adjustment and centrifugation steps).

III. Animal Feed

Animal feed refers to any foodstuff used to feed domesticated livestock (e.g., cattle, goats, sheep, horses, poultry, buffalo, alpaca, llamas, donkeys, mules, rabbits, chickens, geese, turkeys, or pigs). Animal feeds often include hay, straw, silage, compressed and pelleted feeds, oils and mixed rations, and also sprouted grains and legumes. The worldwide animal feed industry consumed 635 million tons of feed in 2006, with an annual growth rate of about 2%. The use of agricultural land to grow feed rather than human food can be controversial; some types of feed, such as corn (maize), can also serve as human food, while others such as grass cannot. In addition to providing an energy source to animals, animal feeds also provide nutrients (e.g. selenium) utilized by the body.

In some embodiments, the invention provides nutritional compositions (e.g. soluble selenium compositions (e.g. SGPs) that permit generation of animal feed compositions comprising selenium (e.g. elevated concentrations of selenium over standard feed compositions (e.g. soluble selenium)) that decreases overall costs, increases feed conversion and maintains and/or improves quality of animal products (e.g. meat, eggs, dairy, etc.) derived from livestock receiving the same compared to conventional animal feeds.

For example, in some embodiments, the invention provides a dietary supplement composition comprising SGPs that can be combined with and/or incorporated into an animal feed and administered to (e.g., fed to) an animal to provide equivalent or superior effects on growth performance in the animal (e.g., compared to animals fed diets with other forms of supplemental selenium (e.g., selenium enriched yeast (e.g., SEL-PLEX)). In some embodiments, a dietary supplement composition of the invention increases the amount of circulating selenium (e.g., located in the blood and/or serum) in a subject (e.g. human or animal) receiving the composition. In some embodiments, a greater proportion of administered selenium is bioavailable in the soluble selenium compositions of the invention (e.g., SGPs) than in other selenium formulations (e.g. sodium selenite or selenium enriched yeast (e.g. SEL-PLEX)). That is, in some embodiments, the invention provides compositions comprising selenoglycoproteins that contain a higher proportion and/or ratio of selenium that is made available (e.g., bioavailable) to a subject compared to other forms of selenium (e.g., selenium enriched yeast) meaning that lesser amounts of a composition comprising selenoglycoprotein of the invention are needed (e.g., to obtain similar bioavailability amounts). In some embodiments, a dietary supplement composition of the invention (e.g., comprising SGPs of the invention) increases the amount of selenium (e.g., located in muscle or, other tissue) in a subject (e.g. human or animal) receiving the composition. In some embodiments, SGPs and/or soluble selenium administration results in increased selenium bioavailability to serum, adipose tissue, muscle tissue, etc.

In some embodiments, the invention provides a method of increasing the efficiency by which an animal utilizes nutrients in a diet fed to the animal comprising providing to the animal a diet comprising a dietary supplement composition of the invention, wherein the supplement composition enhances the animal's ability to process and utilize the nutrients present in their diet. In some embodiments, a dietary supplement composition of the invention increases the amount of circulating antioxidants (e.g., selenium located in the blood and/or serum) in a subject receiving the composition. In some embodiments, a dietary supplement composition of the invention increases the amount of antioxidants (e.g., selenium located in adipose tissue, muscle, etc.) in a subject receiving the composition.

IV. Pharmaceuticals, Nutriceuticals, and Supplements

Nutritional selenium levels have been established by the FDA (See 21 C.F.R. 101.9(c)(8)(iv), January 1994). Humans and animals can safely metabolize limited amounts of both inorganic and organic forms of selenium and can convert non-methylated selenium to mono- or di- or trimethylated derivatives, of which the monomethylated derivatives are most toxic. (See, e.g., Bedwal, R. S., et al., Medical Hypotheses, 41 (2):150-159 (August 1993)). The FDA has adopted Reference Daily Intakes (RDIs) of 70 micrograms for selenium for lactating women and RDI of 55 micrograms for non-lactating adults. Selenium dosage of 600 micrograms per day has been reported as safe. (See, e.g., Ferris G. M. Lloyd, et al., App. Clin. Biochem., 26:83-88 (1989). At about this dosage, normal activity of the enzyme glutathione reductase safely converts selenogluthatione to hydrogen selenide in the liver and erythrocytes and is ultimately excreted. Thus, at such lower dosages, the body is able to safely metabolize and excrete selenium that is present in a free metallic form. However, as with many trace elements (e.g., selenium), at higher dosage levels or concentrations the beneficial effects are reversed and dangerous toxicity is manifested. (See, e.g., Furnsinn, C. et al., Internat'l J. of Obesity and Related Metab. Dis., 19(7):458-463 (1995)).

The administration of selenium in the natural form involves a scientific and medical trade-off because, when administered in relatively low concentrations, selenium provides beneficial health effects, however, at higher concentrations, selenium exhibits dramatic toxicity such that the potential health benefits are lost and toxicity becomes the primary concern.

As described above, the invention provides certain forms of selenium (e.g., SGPs, water-soluble selenium) that provide beneficial effects to a subject. Evidence has shown that organic forms of selenium (e.g., selenomethionine and selenium enriched yeast) may be less toxic and better absorbed than inorganic forms (See, e.g., Mahan, Proceedings of the 15th Annual Symposium Nottingham University Press, Nottingham, UK, pp. 523-535 (1999). Nonetheless, in some embodiments, multiple forms of selenium are used in combination with one another (e.g. to provide beneficial health effects to a subject). Natural sources of selenium include, but are not limited to, selenium enriched (e.g., selenized) yeast. The yeast strain used is not limiting.

In certain preferred embodiments of the invention, SGPs (e.g. derived from selenium enriched yeast (e.g. SEL-PLEX), as described in Examples 1-2) is the selenium form of choice for formulations and compositions of the invention. In some embodiments, compositions comprising water-soluble selenium and/or SGPs provide a more biologically available form of selenium compared to other forms of selenium. However, other forms of selenium may also find use in the invention including derivative or modifications of water-soluble selenium and/or SGPs, SEL-PLEX, or other forms of selenium enriched yeast, selenomethionine, selenocysteine, a selenite compound, a selenate compound, or derivatives, salts, or modifications thereof. Thus, in some preferred embodiments, each of these forms of selenium may be used as a component of a formulation. Alternatively, each of the above described forms of selenium may be linked (e.g., chemically or physically) to a drug or therapeutic to form a selenium-drug derivative. Additionally, compositions and formulations are not limited to one form of selenium. Indeed, a composition or formulation may comprise multiple forms of selenium (e.g., SGPs and SEL-PLEX, or Sod-sel and water-soluble selenium).

Other forms of selenium that find use in various embodiments of the present invention are described in U.S. Pat. Nos. 6,911,550 6,197,295, 5,221,545, 6 and 6,576,233, and U.S. Pat. App. Nos. 20010043925, 20050069594, 20050089530, and 20080107755, herein incorporated by reference in their entireties.

Accordingly, the present invention provides pharmaceutical, nutriceutical, and/or supplement compositions (e.g., foodstuff and/or dietary composition or treatment) that comprise one or more forms of selenium (e.g. SGPs, soluble selenium (e.g. water soluble selenium), etc.), alone or in combination with at least one other agent, such as a stabilizing compound, other therapeutic(s), nutrient(s), and or/minerals; and may be administered in any sterile, biocompatible carrier, including, but not limited to, saline, buffered saline, dextrose, water, etc.

The methods of the present invention find use in treating (e.g., prophylacticly or therapeutically) diseases (e.g., neurodegenerative disease, cancer, etc.) or altering physiological states. Selenium (e.g., soluble selenium (e.g. water-soluble selenium), SGPs))) can be administered to a subject (e.g., a patient) intravenously in a pharmaceutically acceptable carrier such as physiological saline. Standard methods for intracellular delivery of compounds can be used (e.g., delivery via liposome). Such methods are well known to those of ordinary skill in the art. The formulations of this invention are useful for parenteral administration, such as intravenous, subcutaneous, intramuscular, and intraperitoneal. In some embodiments, compositions (e.g., SGPs and/or pharmaceutical formulations comprising the same) are administered orally.

As is well known in the medical arts, dosages for any one subject may depend upon many factors, including the patient's size, body surface area, age, the particular compound to be administered, sex, time and route of administration, general health, and interaction with other drugs being concurrently administered.

Accordingly, in some embodiments compositions and/or formulations comprising selenium (e.g., soluble selenium (e.g. water-soluble selenium), SGPs, etc.) are administered to a subject alone, or in combination with other forms of selenium, drugs, small molecules, or in pharmaceutical compositions where it is mixed with excipient(s) or other pharmaceutically acceptable carriers. In some embodiments, the pharmaceutically acceptable carrier is pharmaceutically inert. In other embodiments, compositions comprising selenium (e.g., soluble selenium (e.g. water-soluble selenium), SGPs, etc.) are administered alone to individual subjects suffering from a disease or condition. In other embodiments of the present invention, compositions comprising selenium (e.g., soluble selenium (e.g. water-soluble selenium), SGPs, etc.) are administered alone to individual subjects for the promotion of general health or the health of a body system. Compositions comprising selenium (e.g., soluble selenium (e.g. water-soluble selenium), SGPs, etc.) alone or in combination with one or more other forms of selenium may be added to a nutritional drink or food (e.g., ENSURE, POWERBAR, or the like), a multi-vitamin, nutritional products, food products, etc. for daily consumption.

Depending on the target sought to be altered by treatment (e.g., gene expression associated with aging, and/or the regulation of gene expression associated with cancer and/or tumor growth or metastasis), these pharmaceutical, supplement, and/or nutriceutical compositions are formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, selenium-containing compositions (e.g. soluble selenium (e.g. water-soluble selenium), SGPs, etc.) are formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the selenium-containing compositions (e.g. soluble selenium (e.g. water-soluble selenium), SGPs, etc.) are formulated using pharmaceutically acceptable carriers well known in the art in dosages suitable for oral administration. Such carriers enable the selenium-containing compositions (e.g. soluble selenium (e.g. water-soluble selenium), SGPs, etc.) to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients (e.g., selenium-containing compositions (e.g. soluble selenium (e.g. water-soluble selenium), SGPs, etc.) are contained in an effective amount to achieve the intended purpose. For example, an effective amount of the pharmaceutical agent may be that amount that alters the expression of a specific gene (e.g., KTLG, GRB2, DNAJ3, TGFB1, MAPK8, C1R, UBE4A, SMPX, USP22, and/or PTP4A1). Determination of effective amounts is well within the capability of those skilled in the art.

The invention also provides pH dependent SGPs and compositions comprising the same for use in the prevention and/or therapeutic treatment of cancer (e.g., to prevent or slow cancer/tumor progression and/or metastasis). For example, in a preferred embodiment, a pH dependent SGP fraction of a selenium enriched yeast (e.g., SEL-PLEX) is administered to a subject to regulate the expression (e.g., in a desired way) of a gene associated with cancer growth and/or metastasis). As described herein, certain soluble, SGP fractions have been identified to possess biological properties (e.g., the ability to regulate gene expression) that the parent material from which the soluble, SGP fraction was derived (e.g., selenium enriched yeast (e.g., SEL-PLEX)) does not possess (See, e.g., Example 4 and FIGS. 7-11). In a preferred embodiment, the pH dependent SGP fraction of a selenium enriched yeast (e.g., SEL-PLEX) is a pH 4.0 dependent fraction, although other fractions (e.g., pH 3.0, pH 6.0, etc.) also find use in the compositions and methods of the invention.

In addition to the active ingredients these selenium-containing (e.g. soluble selenium (e.g. water-soluble selenium), SGPs, etc.) pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For compositions or formulations comprising selenium, conditions indicated on the label may include treatment of condition related to prophylactic or therapeutic treatment of a disease or condition (e.g., cancer, neurodegenerative disease and/or cognitive function).

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the methods of the invention, the therapeutically effective dose can be estimated initially from cell culture assays. Then, preferably, dosage can be formulated in animal models (particularly murine models) to achieve a desirable circulating concentration range.

A therapeutically effective dose refers to that amount of which ameliorates or prevents symptoms of a disease state or condition (e.g., through altering gene expression). Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds which exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage may be chosen by a subject or by a physician in view of the patient to be treated. Dosage and administration are adjusted to provide sufficient levels of the active moiety or to maintain the desired effect (e.g., alteration of gene expression in a subject). Additional factors that may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks or once every month depending on half-life and clearance rate of the particular formulation.

In some embodiments, selenium (e.g., soluble selenium, water-soluble selenium, SGPs, etc.) is administered at a daily dose of between 25 and 600 μg per day (e.g., soluble selenium, water-soluble selenium, and/or SGP is administered to a subject in such a way so as to provide between 25 and 600 μg of selenium to the subject each day). In preferred embodiments, the selenium is administered at a daily dose of between 50 and 200 μg per day. In other preferred embodiments, selenium is administered at a daily dose of between 100 and 200 μg per day. Doses outside of 25 and 600 μg may be used. In some embodiments, a single dose of selenium (e.g., soluble selenium, water-soluble selenium, SGPs, etc.) is administered once daily. In other embodiments, 2, 3, 4, or more doses may be administered each day (e.g., once in the morning and once at night, or once every 4 to 6 hours). For example, in some embodiments, selenium (e.g., soluble selenium, water-soluble selenium, SGPs, etc.) is administered to a subject in three separate, more than three separate, two separate, or less than two separate doses. In some preferred embodiments, the daily dose is administered in a time release capsule. In some preferred embodiments, the daily dose is between 25-75 μg of selenium (e.g., soluble selenium, water-soluble selenium, SGPs, etc.). In other preferred embodiments, the daily dose is 200 μg of selenium (e.g., organic selenium, selenized yeast, SEL-PLEX, soluble selenium, water-soluble selenium, SGPs, etc.).

The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Compositions and formulations comprising selenium are believed to be particularly useful for oral administration.

Selenium-containing (e.g. SGP-containing) pharmaceutical, nutriceutical, and/or supplement compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Thus, in some embodiments, pharmaceutical, nutriceutical, and/or supplement compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical, nutriceutical, and/or supplement formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

In some embodiments, the selenium-containing (e.g. soluble selenium, water-soluble selenium, SGP) compositions of the present invention may be formulated into any of many possible dosage forms such as, but not limited to, tablets, capsules, liquid syrups, soft gels, suppositories, and enemas. The compositions of the present invention may also be formulated as time-release nanoparticles (e.g. nanocapsules), vesicles, liposomes, polymers (e.g. molecularly imprinted polymers (MIPs), biodegradable slow-release polymers, polycationic polymers, etc. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers. In one embodiment of the present invention the pharmaceutical, and/or supplement compositions may be formulated and used as foams. Foams include formulations such as, but not limited to, emulsions, microemulsions, creams, jellies and liposomes. While basically similar in nature these formulations vary in the components and the consistency of the final product.

The selenium-containing (e.g. soluble selenium, water-soluble selenium, SGP, etc.) compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

In some embodiments, the invention provides pharmaceutical, nutriceutical, and/or supplement compositions containing (a) one or more forms of selenium (e.g., SGP (e.g., pH dependent SGP fraction), soluble selenium, water-soluble selenium, SEL-PLEX) and (b) one or more other agents (e.g., nutrient, mineral, therapeutic, etc.).

The present invention also includes methods involving co-administration of compounds comprising selenium (e.g. soluble selenium, water-soluble selenium, SGP, etc.) described herein with one or more additional active agents (e.g., a therapeutic (e.g., cancer therapeutic, Alzheimer's therapeutic), anti-oxidant, etc.). Indeed, it is a further aspect of this invention to provide methods for enhancing therapies and/or pharmaceutical, nutriceutical, and/or supplement compositions by co-administering a composition comprising selenium (e.g. soluble selenium, water-soluble selenium, SGP (e.g., pH dependent SGP fraction), etc.) of this invention with a preventative or therapeutic pharmaceutical composition, nutriceutical and/or supplement. In co-administration procedures, the agents may be administered concurrently or sequentially. In one embodiment, the compounds described herein are administered prior to the other active agent(s). The formulations and modes of administration may be any of those described above. In addition, the two or more co-administered agents may each be administered using different modes or different formulations. In some embodiments, a composition of the invention is co-administered with a cancer treatment.

Accordingly, in some embodiments, a composition containing one or more forms of selenium (e.g., SGP (e.g., pH dependent SGP fraction), soluble selenium, water-soluble selenium, SEL-PLEX) is administered systemically or locally to inhibit tumor cell proliferation and angiogenesis, and/or induce tumor cell death in cancer patients. For example, in some embodiments, a composition comprising a pH dependent SGP fraction (pH 4.0) of a selenium enriched yeast (e.g., SEL-PLEX) is administered to a subject under conditions such that the expression of one or more genes associated with cancer/tumor growth and/or metastasis is regulated (e.g., upregulated or downregulated) in a beneficial manner in the subject (See, e.g., Example 4). The compositions can be administered intravenously, intrathecally, intraperitoneally as well as orally. Moreover, they can be administered alone or in combination with anti-proliferative drugs.

Where combinations are contemplated, it is not intended that the present invention be limited by the particular nature of the combination. The present invention contemplates combinations as simple mixtures as well as chemical hybrids. An example of the latter is where a composition containing one or more forms of selenium is covalently linked to a targeting carrier or to an active pharmaceutical. Covalent binding can be accomplished by any one of many commercially available crosslinking compounds.

It is not intended that the present invention be limited by the particular nature of the therapeutic preparation. For example, such compositions can be provided together with physiologically tolerable liquid, gel or solid carriers, diluents, adjuvants and excipients.

These therapeutic preparations can be administered to mammals for veterinary use, such as with domestic or farm raised animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as liquid solutions or suspensions, or in solid forms. Oral formulations for cancer usually will include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%-95% of active ingredient, preferably 2%-70%.

The compositions are also prepared as injectables, either as liquid solutions or suspensions; solid forms suitable for solution in, or suspension in, liquid prior to injection may also be prepared.

The compositions of the present invention are often mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

A wide range of therapeutic agents find use with the present invention. For example, any therapeutic agent that can be co-administered with a composition containing one or more forms of selenium of the invention is suitable for use in the present invention.

Some embodiments of the present invention provide administering to a subject an effective amount of a composition containing one or more forms of selenium and at least one anticancer agent (e.g., a conventional anticancer agent, such as, chemotherapeutic drugs, and/or radiation therapy).

Anticancer agent mechanisms suitable for use with the present invention include, but are not limited to, agents that induce apoptosis, agents that induce/cause nucleic acid damage, agents that inhibit nucleic acid synthesis, agents that affect microtubule formation, and agents that affect protein synthesis or stability.

Classes of anticancer agents suitable for use in compositions and methods of the present invention include, but are not limited to: 1) alkaloids, including, microtubule inhibitors (e.g., Vincristine, Vinblastine, and Vindesine, etc.), microtubule stabilizers (e.g., Paclitaxel (Taxol), and Docetaxel, etc.), and chromatin function inhibitors, including, topoisomerase inhibitors, such as, epipodophyllotoxins (e.g., Etoposide (VP-16), and Teniposide (VM-26), etc.), and agents that target topoisomerase I (e.g., Camptothecin and Isirinotecan (CPT-11), etc.); 2) covalent DNA-binding agents (alkylating agents), including, nitrogen mustards (e.g., Mechlorethamine, Chlorambucil, Cyclophosphamide, Ifosphamide, and Busulfan (Myleran), etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents (antitumor antibiotics), including, nucleic acid inhibitors (e.g., Dactinomycin (Actinomycin D), etc.), anthracyclines (e.g., Daunorubicin (Daunomycin, and Cerubidine), Doxorubicin (Adriamycin), and Idarubicin (Idamycin), etc.), anthracenediones (e.g., anthracycline analogues, such as, (Mitoxantrone), etc.), bleomycins (Blenoxane), etc., and plicamycin (Mithramycin), etc.; 4) antimetabolites, including, antifolates (e.g., Methotrexate, Folex, and Mexate, etc.), purine antimetabolites (e.g., 6-Mercaptopurine (6-MP, Purinethol), 6-Thioguanine (6-TG), Azathioprine, Acyclovir, Ganciclovir, Chlorodeoxyadenosine, 2-Chlorodeoxyadenosine (CdA), and 2'-Deoxycoformycin (Pentostatin), etc.), pyrimidine antagonists (e.g., fluoropyrimidines (e.g., 5-fluorouracil (Adrucil), 5-fluorodeoxyuridine (FdUrd) (Floxuridine)) etc.), and cytosine arabinosides (e.g., Cytosar (ara-C) and Fludarabine, etc.); 5) enzymes, including, L-asparaginase, and hydroxyurea, etc.; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole (Arimidex), etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15)

tumor vaccines; 16) therapies directed against tumor metastases (e.g., Batimistat, etc.); and 17) other inhibitors of angiogenesis.

In preferred embodiments, the present invention provides administration of an effective amount of a composition containing one or more forms of selenium of the invention and at least one conventional anticancer agent that induces apoptosis and/or prevents cancer cell proliferation to a subject. In some preferred embodiments, the subject has a disease characterized by metastasis. In yet other preferred embodiments, the present invention provides administration of an effective amount of a compositions containing one or more forms of selenium and a taxane (e.g., Docetaxel) to a subject having a disease characterized by the overexpression of Bcl-2 family protein(s) (e.g., Bcl-2 and/or Bcl-$X_L$).

The taxanes (e.g., Docetaxel) are an effective class of anticancer chemotherapeutic agents. (See e.g., K. D. Miller and G. W. Sledge, Jr. Cancer Investigation, 17:121-136 (1999)). While the present invention is not intended to be limited to any particular mechanism, taxane-mediated cell death is thought to proceed through intercellular microtubule stabilization and subsequent induction of the apoptotic pathway. (See e.g., S. Haldar et al., Cancer Research, 57:229-233 (1997)). In some other embodiments, cisplatin and taxol are specifically contemplated for use with a composition containing one or more forms of selenium of the present invention. In some embodiments, any pharmaceutical that is routinely used in a cancer therapy context finds use in the present invention. Conventional anticancer agents that are suitable for administration with the disclosed compositions containing one or more forms of selenium include, but are not limited to, adriamycin, 5-fluorouracil, etoposide, camptothecin, methotrexate, actinomycin-D, mitomycin C, or more preferably, cisplatin. In some embodiments of the present invention, therapeutic treatments further comprise one or more agents that directly cross-link nucleic acids (e.g., DNA) to facilitate DNA damage leading to a synergistic, antineoplastic agents of the present invention. For example, agents such as cisplatin, and other DNA alkylating agents may be used. Agents that damage DNA also include compounds that interfere with DNA replication, mitosis, and chromosomal segregation. Such chemotherapeutic compounds include, but are not limited to, adriamycin, also known as doxorubicin, etoposide, verapamil, podophyllotoxin, and the like. These compounds are widely used in clinical settings for the treatment of neoplasms, and are administered through bolus injections intravenously at doses ranging from 25-75 M/$^2$ at 21 day intervals for adriamycin, to 35-50 Mg/M$^2$ for etoposide intravenously or double the intravenous dose orally.

Agents that disrupt the synthesis and fidelity of nucleic acid precursors and subunits also lead to DNA damage and find use as chemotherapeutic agents in the present invention. A number of nucleic acid precursors have been developed. Particularly useful are agents that have undergone extensive testing and are readily available. As such, agents such as 5-fluorouracil (5-FU) are preferentially used by neoplastic tissue, making this agent particularly useful for targeting to neoplastic cells. The doses delivered may range from 3 to 15 mg/kg/day, although other doses may vary considerably according to various factors including stage of disease, amenability of the cells to the therapy, amount of resistance to the agents and the like.

In preferred embodiments, the anticancer agents (e.g., antiangiogenic factors discussed herein) used in the present invention are those that are amenable to co-administration with a composition containing one or more forms of selenium or are otherwise associated with the composition containing one or more forms of selenium such that they can be delivered into a subject, tissue, or cell without loss of fidelity of anticancer effect. For a more detailed description of cancer therapeutic agents such as a platinum complex, verapamil, podophyllotoxin, carboplatin, procarbazine, mechlorethamine, cyclophosphamide, camptothecin, ifosfamide, melphalan, chlorambucil, bisulfan, nitrosurea, adriamycin, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate and other similar anti-cancer agents, those of skill in the art are referred to any number of instructive manuals including, but not limited to, the Physician's Desk reference and to Goodman and Gilman's "Pharmaceutical Basis of Therapeutics" ninth edition, Eds. Hardman et al., 1996.

V. Antioxidants

In some embodiments of the present invention, antioxidants are co-administered with compositions or formulations of the present invention. The present invention is not limited by the type of antioxidant utilized. Indeed, a variety of antioxidants are contemplated to be useful in the present invention including, but not limited to, alkylated diphenylamines, N-alkylated phenylenediamines, phenyl-.alpha.-naphthylamine, alkylated phenyl-.alpha.-naphthylamine, dimethyl quinolines, trimethyldihydroquinolines and oligomeric compositions derived therefrom, hindered phenolics, alkylated hydroquinones, hydroxylated thiodiphenyl ethers, alkylidenebisphenols, thiopropionates, metallic dithiocarbamates, 1,3,4-dimercaptothiadiazole and derivatives, oil soluble copper compounds, and the like, Naugalube® 438, Naugalube 438L, Naugalube 640, Naugalube 635, Naugalube 680, Naugalube AMS, Naugalube APAN, Naugard PANA, Naugalube TMQ, Naugalube 531, Naugalube 431, Naugard BHT, Naugalube 403, and Naugalube 420, ascorbic acid, tocopherols including alpha-tocopherol, water-soluble antioxidants such as sulfhydryl compounds and their derivatives (e.g., sodium metabisulfite and N-acetyl-cysteine), lipoic acid and dihydrolipoic acid, resveratrol, lactoferrin, ascorbic acid derivatives (e.g., ascorbyl palmitate and ascorbyl polypeptide), butylated hydroxytoluene, retinoids (e.g., retinol and retinyl palmitate), tocotrienols, ubiquinone, extracts containing flavonoids and isoflavonoids and their derivatives (e.g., genistein and diadzein), extracts containing resveratrol and the like, grape seed, green tea, pine bark, propolis, Irganox1010, 1035, 1076, 1222 (manufactured by Ciba Specialty Chemicals Co., Ltd.), Antigene P, 3C, FR, Sumilizer GA-80 (manufactured by Sumitomo Chemical Industries Co., Ltd.), beta-carotene, lycopene, vitamins C, E, and A, and other substances.

Although an understanding of the mechanism is not necessary to practice the present invention and the present invention is not limited to any particular mechanism of action, in some embodiments, administering a selenium-containing composition (e.g. soluble selenium, SGP) to a subject changes gene expression profiles (e.g., TGFB1, MAPK8, C1R, UBE4A, SMPX, USP22, and PTP4A1) in the subject. In some embodiments, administering a selenium-containing composition (e.g. soluble selenium, SGP) to a subject reduces the level of DNA damage (e.g. in brain tissue (e.g., neocortex), muscle tissue, adipose tissue, etc.) of a subject.

In some embodiments, the present invention provides a method of reducing sensitivity of cells to $H_2O_2$ cytotoxicity comprising administering to the cells a selenium-containing composition (e.g. soluble selenium, water-soluble selenium, SGP, SEL-PLEX, etc.).

The invention further provides a method of reducing superoxide radicals in a subject (e.g., in a subject experiencing oxidative stress) comprising administering a composition (e.g., a nutritional supplement) comprising selenium (e.g. soluble selenium, water-soluble selenium, SGP, SEL-PLEX, etc.) to the subject. Furthermore, in some embodiments, the present invention provides that subjects receiving certain compositions comprising selenium (e.g. soluble selenium, water-soluble selenium, SGP, SEL-PLEX, etc.) have an enhanced ability to deal with oxidative stress. Although an understanding of the mechanism is not necessary to practice the present invention and the present invention is not limited to any particular mechanism of action, in some embodiments, subjects receiving a composition comprising selenium (e.g., a dietary supplement comprising selenium (e.g. soluble selenium, water-soluble selenium, SGP, SEL-PLEX, etc.)) have an enhanced ability to cope with oxidative stress due to the ability of select forms of selenium (e.g. soluble selenium, water-soluble selenium, SGP, SEL-PLEX, etc.) to alter (e.g., reduce) the level of superoxide radicals in the subject.

It is contemplated that the compositions and methods of the present invention will find use in various settings, including, but not limited to, research and clinical diagnostics.

VI. Carriers

In some embodiments, the present invention provides delivery of selenium (e.g. selenoglycoprotein) via one or more carriers including, but not limited to nanoparticles (e.g. nanocapsules), vesicles, liposomes, polymers (e.g. molecularly imprinted polymers (MIPs), slow-release polymers, polycationic polymers, and/or polymerosomes. In some embodiments, a selenium carrier provides administration, targeting, and/or timed release of selenium-containing compounds (e.g. water-soluble selenium, SGP) in a subject (e.g. human or animal). In some embodiments, carriers (e.g. slow-release polymer, nanocapsule, MIP, polymerosomes, etc.) enhance delivery of selenium-containing compounds (e.g. organic selenium, soluble selenium, water-soluble selenium, SGP, SEL-PLEX, etc.) to a subject. In some embodiments, carriers (e.g. slow-release polymer, nanocapsule, MIP, polymerosomes, etc.) increase the bioavailability of selenium-containing compounds (e.g. organic selenium, soluble selenium, water-soluble selenium, SGP, SEL-PLEX, etc.) to a subject.

The invention is not limited by the type of carrier utilized. Indeed a variety of carriers may be used including, but not limited to, dendrimers, polymerosomes, nanoparticles, slow-release polymers, nanocapsules, molecularly imprinted polymers and/or other type of carrier (e.g., any one of the carriers described herein). In one preferred embodiment, the carrier is a slow-release polymer. In another preferred embodiment, the carrier is a molecularly imprinted polymer. In still another preferred embodiment, the carrier is a polymersome used to encapsulate selenoglycoprotein. The invention is not limited by the type of polymersome used. Indeed, any polymersome known in the art may be utilized. In some embodiments, the polymersome comprises poly(ethylene oxide) (PEO) block copolymer. However, the invention is not so limited. Any known block copolymer may be utilized, including, for example poly(ethylethylene) (PEE), poly(butadiene) (PB or PBD), poly(styrene) (PS), and poly(isoprene) (PI). In some embodiments, the polymer comprises poly(ε-caprolactone) (PCL) diblock co-polymer. In some embodiments, the polymersome comprises poly(ethylene oxide)-block-poly(ε-caprolactone) (PEO-b-PCL) based diblock copolymers. In some embodiments, the polymersome comprises a block copolymer that is a triblock, tetrablock, pentablock, or at least six block copolymer. In some embodiments, the polymersome is derived from the coupling of poly(lactic acid), poly(glycolide), poly(lactic-coglycolic acid) and/or or poly(3-hydroxybutyrate) with PEO. The invention is not limited by the size of a polymersome encapsulated selenoglycoprotein. A variety of sizes find use in the compositions and methods of the invention including, but not limited to, polymersome encapsulated selenoglycoproteins that are about, 50-300 nm in diameter although larger (e.g., about 350 nm, 400 nm, 500 nm or larger) and smaller (e.g., about 40 nm, 30 nm, 20 nm, or smaller) polymersome encapsulated selenoglycoproteins may be used.

In some embodiments, the present invention comprises SGP controlled-release nanocapsules and MIP spheres to provide steady and safe supply of organic selenium (e.g. molecularly imprinted polymers (MIPs), slow-release polymers, etc.) in comparison with other forms of selenium (e.g. selenium enriched yeast, SEL-PLEX, or inorganic selenium single doses capsules or pills). In some embodiments, water-soluble, soluble, and/or SGPs are utilized for efficient encapsulation and delivery of selenium through the advanced delivery methods herein (e.g. nanoparticles (e.g. nanocapsules), vesicles, polymers (e.g. molecularly imprinted polymers (MIPs), slow-release polymers, etc.), and/or polymerosomes). In some embodiment, the advanced delivery methods herein enhance the bioavailability of the encapsulated selenium (e.g. SGPs or soluble selenium). In some embodiments, the advanced delivery methods herein provide slow-release (e.g. 12 hours, 24 hours, 2 days, 1 week, 2 weeks, 3 weeks, 10 weeks, etc.) of selenium into a solution, a subject, serum, etc.

In some embodiments, the invention provides slow-release polymers as a carrier for selenium-containing compositions (e.g. organic selenium, soluble selenium, water-soluble selenium, SGP, etc.) of the present invention. Slow release polymers, such as poly(lactic acid-co-glycolic acid) (PLGA), or polycationic polymers, such as, polyethyleneimine (PEI), may be utilized as carriers. In some embodiments, slow-release polymers provide controlled delivery of selenium containing compositions (e.g. organic selenium, soluble selenium, water-soluble selenium, SGP, SEL-PLEX, etc.). In some embodiments, controlled delivery occurs when a polymer (e.g. PEI), whether natural or synthetic, is judiciously combined with a selenium-containing composition (e.g. organic selenium, soluble selenium, water-soluble selenium, SGP, SEL-PLEX, etc.) and optionally other active or inactive agents in such a way that the selenium-containing composition (e.g. organic selenium, soluble selenium, water-soluble selenium, SGP, SEL-PLEX, etc.) is released from the material in a predesigned manner. The release of the selenium-containing composition (e.g. organic selenium, soluble selenium, water-soluble selenium, SGP, SEL-PLEX, etc.) may be constant over a long period, it may be cyclic over a long period, or it may be triggered by the environment or other external events. In some embodiments, controlling delivery provides more effective therapy. In some embodiments, controlling delivery eliminates the potential for both under- and overdosing. Other advantages of using controlled-delivery systems can include the maintenance of selenium levels within a desired range, the need for fewer administrations, and increased patient compliance.

In some embodiments, the invention provides polymerosomes as carriers for selenium-containing compositions (e.g. organic selenium, soluble selenium, water-soluble selenium, SGP, SEL-PLEX, etc.) of the present invention. In some embodiments, polymersomes are made using amphiphilic synthetic block copolymers to form the vesicle membrane, and have radii ranging from about 50 nm to about 10 um or more (See, e.g., Discher et al. Journal of Physical Chemistry B (2002), 106(11), 2848-2854), herein incorporated by reference in its entirety). In some embodiments, polymersomes contain an aqueous solution in their core and are useful for encapsulating and protecting molecules, such as selenium-containing compositions (e.g. organic selenium, soluble selenium, water-soluble selenium, SGP, SEL-PLEX, etc.) and optionally one or more of drugs, enzymes, other proteins and peptides, and DNA and RNA fragments. In some embodiments, the polymersome membrane provides a physical barrier that isolates the encapsulated material from external materials, such as those found in biological systems. In some embodiments, polymerosomes allow timed release of contents within their core (e.g. selenium-containing compositions (e.g. organic selenium, soluble selenium, water-soluble selenium, SGP, SEL-PLEX, etc.)). In some embodiments, the use of synthetic polymers to construct polymerosomes enables designers to manipulate the characteristics of the membrane and thus control permeability, release rates, stability and other properties.

In one embodiment, the selenium-containing (e.g. soluble selenium, water-soluble selenium, SGP) compositions of the present invention may be encapsulated inside poly(ethylene oxide)-block-poly(ε-caprolactone) (PEO-b-PCL) based polymersomes. Although an understanding of a mechanism is not necessary to practice the invention, and the invention is not limited to any particular mechanism of action, in some embodiments, PEO provides the resultant carrier improved in vitro chemical and mechanical stability, augmented in vivo bioavailability and prolonged blood circulation half-lives. PCL, a well-known implantable biomaterial, forms the polymersome membrane, and facilitates complete and safe in vivo degradation of resulting product by hydrolysis of its ester linkages.

In another embodiment, the selenium-containing compositions (e.g., selenoglycoproteins) of the present invention may be encapsulated in polymersomes synthesized from blends or pure derivatives of other biodegradable block polymers derived from the coupling of poly(lactic acid), poly (glycolide), poly(lactic-coglycolic acid) or poly(3-hydroxybutyrate) with PEO.

In some embodiments, the present invention provides nanocapsules (Couvreur et al. Crit. Rev Ther Drug Carrier Syst. 2002; 19(2):99-134, herein incorporated by reference in its entirety) as carriers for selenium-containing compositions (e.g. organic selenium, soluble selenium, water-soluble selenium, SGP, SEL-PLEX, etc.) of the present invention (See, e.g., U.S. Pat. No. 7,498,045, herein incorporated by reference in its entirety). In some embodiments, nanocapsules provide controlled release of selenium-containing compositions (e.g. organic selenium, soluble selenium, water-soluble selenium, SGP, SEL-PLEX, etc.) upon biodegradation of the nanocapsule. In some embodiments, nanocapsules have biodegradation half-lives of about 2 to about 100 hours (e.g. about 2 hours . . . 4 hours . . . 6 hours . . . 12 hours . . . 24 hours . . . 48 hours . . . 96 hours, etc.). In some embodiments, biodegradable nanocapsules of the invention are adaptable for the controlled release of selenium-containing compositions (e.g. organic selenium, soluble selenium, water-soluble selenium, SGP, SEL-PLEX, etc.) and optionally a variety of other encapsulated therapeutic agents, including macromolecules, into in vivo circulation of a subject upon administration thereto. The nanocapsule compositions of the present invention are further adapted to encapsulate therapeutically effective concentrations of selenium-containing compositions (e.g. organic selenium, soluble selenium, water-soluble selenium, SGP, etc.) and deliver the same into in vivo circulation of a recipient. In some embodiments, a nanocapsule encapsulates selenium-containing compositions (e.g. organic selenium, soluble selenium, water-soluble selenium, SGP, SEL-PLEX, etc.) is a membrane comprising, for example, a copolymer of polylactic acid polymer and polyethylene glycol. In some embodiments, nanocapsules are formed by the interfacial polymerization of a monomer or the interfacial nanodeposition of a preformed polymer.

In some embodiments, the present invention provides molecularly imprinted polymers as carriers for selenium-containing compositions (e.g. organic selenium, soluble selenium, water-soluble selenium, SGP, SEL-PLEX, etc.) of the present invention (Mosbach. Trends in Biochemical Sciences, Vol. 7, pp. 92-96, 1994., Wulff. Trends in Biotechnology, Vol. 11, pp. 85-87, 1993., Andersson, et al., Molecular Interactions in Bioseparations (Ngo. T. T. ed.), pp. 383-394)., U.S. Pat. No. 5,959,050, herein incorporated by reference in their entireties

EXPERIMENTAL

The following examples are provided in order to demonstrate and further illustrate certain preferred embodiments and aspects of the present invention and are not intended to be construed as limiting the scope thereof.

Example 1

A. Sequential Preparation of Soluble Selenoglycoproteins from SEL-PLEX by Acidic Extraction and Subsequent Precipitations A 4 L three neck reactor (extractor#1, See FIG. 1) equipped with a mechanical stirrer, a thermometer, and an electric blanket was filled with 3 L of deionized $H_2O$ and 50 ml of 0.3N HCl. The reactor was heated to above 50° C. and 600 g of SEL-PLEX at 1600 ppm was added in portions while stirring. After approximately an hour, the temperature reached 80° C. and the pH of the mixture was 2.23. The pH was reduced to 1.5 by the addition of 13.5 mL of 0.3N HCl. The reaction vessel was maintained with heating and stirring for 7 hrs. The pH of the mixture was checked approximately every hour to ensure the pH level remained at 1.5. The acidic post-reaction mixture (pH 1.5) was distributed into four 1 L centrifuge jars and centrifuged (centrifuge#1, See FIG. 1) at 4000 RCF for 20 min at 8° C. The supernatant (pH 1.5) and the solids pellet were collected. The supernatant was added to a 3 L 3-neck reactor (mixer#1, See FIG. 1) in an ice-bath (4° C.), and equipped with a dropping funnel containing 2N NaOH, a mechanical stirrer and a pH electrode. 2N NaOH was added drop wise to the solution while stirring until the pH of the mixture reached 1.85. During the addition of NaOH, a white precipitate was formed. Stirring continued for 30 min and the mixture was centrifuged again (centrifuge#2, See FIG. 1) forming a supernatant and a selenoglycoprotein pellet. The selenoglycoprotein pellet was collected and freeze-dried (freeze-drier#1, See FIG. 1) yielding 1.635 g of white precipitate. The supernatant at pH 1.85 and the pellet formed at pH 1.5 was added to a reaction vessel (mixer#2, See FIG. 1) and placed in an ice-water bath (4° C.). The mixture was stirred for 30 minutes and then centrifuged (centrifuge#3, See FIG. 1 and FIG. 2), forming wet residue solids and a supernatant at pH 1.6, later used to generate SGPs by subsequent pH-dependent precipitation (e.g., pH 3.0, pH 4.0 and pH 6.0 SGP fractions as described below).

B. pH Dependent Precipitation of Selenoglycoproteins

The supernatant of pH 1.6 was placed in a reactor (mixer #3, See FIG. 2) and 2N NaOH was added to the solution while stirring until the pH of the mixture reached 3.0. Stirring continued for 30 more minutes and the mixture was centrifuged (centrifuge#4, See FIG. 2) forming a supernatant and a selenoglycoprotein pellet. The selenoglycoprotein pellet at pH3.0 (SGP pH 3.0) was collected and freeze-dried (freeze-drier#2, See FIG. 2) yielding a light gray precipitate. The supernatant of pH 3.0 was placed in a reactor (mixer #4, See FIG. 2) and 2N NaOH was added to the solution until the pH of the solution increased to 4.0. Stirring continued for 30 more minutes and the mixture was centrifuged (centrifuge#5, See FIG. 2) forming a supernatant and a selenoglycoprotein pellet. The selenoglycoprotein pellet at pH4.0 (SGP pH 4.0) was collected and freeze-dried (freeze-drier#3, See FIG. 2) yielding the light grey precipitate. The supernatant of pH 4.0 was placed in a reactor (mixer #5, See FIG. 2) and 2N NaOH was added to the solution until the pH of the solution increased to 6.0. Stirring continued for 30 more minutes and the mixture was centrifuged (centrifuge#6, See FIG. 2) forming a supernatant and a selenoglycoprotein pellet. The selenoglycoprotein pellet at pH6.0 (SGP pH 6.0) was collected and freeze-dried (freeze-drier#4, See FIG. 2) yielding the light grey precipitate. Subsequent precipitates that had formed were collected by centrifugation. The waste water stream of pH 6.0 from the last centrifugation contained some seleno-peptides, mannose and glucose oligosaccharides (e.g., that can be utilized in preparation of yeast growth media or other nutrient matter). The process did not produce toxic waste and is environmentally friendly.

Example 2

Soluble SGP Separation and Characterization

The pellet containing solid residues at pH1.5 formed by the acidic extraction of SEL-PLEX was washed with the supernatant at pH 1.85 from the second extraction (SEE Example 1) to reduce the volume of water used in the process, and to dissolve most of the SGP's trapped within the pellet. The solid residues following the third centrifugation at pH 1.6 contain a significant amount of selenium and can be blended with a fresh batch of selenium yeast before being spray-dried, completely utilizing the material that was taken for the extraction.

Total selenium, percent protein concentration, and the weight of each of the SGP fractions were averaged after three subsequent extractions from SEL-PLEX (See Table 1). The extracted SGP fractions constituted from 2.0 to 2.5 weight % of SEL-PLEX and from 4.3 to 5.75% of total selenium that was present in pre-extracted SEL-PLEX.

There was a positive correlation between the pH of the SGP fractions and protein weight, the inverse being true for total selenium concentration (See Table 1).

The average protein weight for the SGP fractions ranged from approximately 65 to 90% weight, and the concentration of selenium for the same set of fractions ranged from approximately 2900 ppm to 4900 ppm range. The SGP fractions contained from 4 to 37 weight % of carbohydrate component.

TABLE 1

The averaged results from three subsequent extractions of 600 g of SEL-PLEX

| Fraction pH | Se concentration [ppm] | Protein weight [%] | Weight [g] |
|---|---|---|---|
| 1.85 | 4887 | 65.55 | 1.635 |
| 3.0 | 3836 | 76.04 | 5.652 |
| 4.0 | 3250 | 87.74 | 3.634 |
| 6.0 | 2915 | 91.81 | 1.757 |

Gel electrophoresis of the SGP fraction at pH1.5 formed by the acidic extraction of SEL-PLEX revealed that bands corresponding to high molecular weight proteins or proteins carrying a large carbohydrate component were absent. Similar size distribution, with domination of low molecular weight fractions, was detected using capillary electrophoresis and the low molecular weight proteins from 5.1 kDa to 12.2 kDa comprised more than 90% of the mixtures.

Size exclusion chromatography of three SGP fractions at pH 3.0, 4.0, and 6.0 on BIO-RAD P10 gel (retention times up to 6 hrs) and on BIO-RAD P30 gel (less than one hour retention time), resulted in an early peak with the retention time 5-10 minutes and a broad, later peak, with the retention time 35-60 minutes. The early peak contained significantly more protein: from 64.74 to 75.24%, and significantly higher selenium concentration: from 2972 to 4252 ppm. The content of protein in the late peak was much lower: from 31.66 to 54.95% and the selenium concentration was significantly lower: from 1193 to 1858 ppm. This type of chromatography can yield SGP's with high content of Se from crude fractions, and demonstrated low homogeneity of the carbohydrate component in these mixtures.

Size exclusion chromatography on SUPERDEX Peptide 10/300 GL resin (AMERSHAM Biosciences; fractionation range 7.0-100 kDa) using 0.1M AcONH4 (pH 7.5) of various peptides from tryptic digestion of SEL-PLEX, have produced similar set of peaks for SGP samples (10-100 kDa and >100 kDa) and completely different elution pattern for the SEL-PLEX sample. Only the "early" peaks, with the elution time below 20 min, contained selenium. The selenium containing eluents were collected, lyophilized and analyzed using SEC ICP MS, MALDI TOF MS and nano ESI MS/MS techniques. The results were complementary and allowed the detection, identification and sequencing of selenium containing peptides. The identification of detected proteins was obtained by SwissProt data base search (See Table 2).

TABLE 2

Identified seleno-peptides and selenoproteins from tryptic digestion of SEL-PLEX extract.

| SEC fraction analyzed | Detected peptide mass ($^{80}$Se) (M + H)$^+$, Th | Identified peptide sequence | Protein | Protein molecular mass (kDa) |
|---|---|---|---|---|
| 2 | 653.39 | GSDTMRSVSPIR SEQ ID NO: 1 | Ylr 190 wp | 42 |
|  | 701.42 | GSDTSeMRSVSPIR SEQ ID NO: 2 |  |  |
| 3 | 637.39 | SGMSKK SEQ ID NO: 3 | Phosphatidylinositol 4 kinase alpha | 89 |
|  | 685.41 | SGSeMSKK SEQ ID NO: 4 |  |  |
| 2 | 587.33 | EVIGIDPSSAMLSIAEK SEQ ID NO: 5 | Yhr209wp | 34 |
|  | 635.35 | EVIGIDPSSASeMLSIAEK SEQ ID NO: 6 |  |  |
| 3 | 637.39 | ASeMIVR SEQ ID NO: 7 | Ribonuclease III | 77 |
| 1 and 2 | 402.10 | DYSeMGAAK SEQ ID NO: 8 | HSP 12 | 12 |
| 1 and 2 | 489.55 | SIVPLSeMDR SEQ ID NO: 9 | HSP 10 | 10 |
| 1 and 2 | 504.03 | SeMGHDQSGTK SEQ ID NO: 10 | SIP 18 | 18 |

The most surprising nature of this method was that the protein composition of various fractions obtained by chromatographic separations (e.g. ion exchange chromatography, size exclusion chromatography) of different SGP fractions from pH dependent precipitation, was the same or very similar, according to electrophoretic methods (gel electrophoresis and capillary electrophoresis) that have been applied. As described herein, extraction of selenoglycoproteins from selenium enriched yeast was successful at a low pH (e.g., 1.5). Although an understanding of a mechanism is not needed to practice the invention and the invention is not limited to any particular mechanism of action, in some embodiments, under the acidic conditions used for SGP extraction, the protein cores are not hydrolyzed significantly and survive mostly in their original form. In some embodiments, pH dependent selenoglycoprotein fractions of SEL-PLEX (e.g., SGP pH 3.0, SGP pH 4.0, SGP pH 6.0) are generated and administered (e.g., by themselves or in combination with another agent) to a subject (e.g., to deliver organic selenium to a subject (e.g., via an oral route)).

Example 3

Bioavailability Comparison

Chicks were fed for eighteen days with seven different dietary treatments (See Tables 3 and 4) to compare the bioavailability of selenium from the pH dependent precipitation of SGP's from SEL-PLEX acidic extract by measuring selenium content in chicken breast muscle:

TABLE 3

Composition and nutrient specification of basal diet

|  | % |
|---|---|
| Ingredient |  |
| Corn | 57.80 |
| Soybean meal (48%) | 35.00 |
| Corn oil | 3.20 |
| Limestone | 1.30 |
| Dicalcium phosphate | 1.80 |
| Salt | 0.45 |
| Vit-Min Mix (no Se) | 0.25 |
| DL-Methionine | 0.20 |
| Total | 100 |
| Nutrient |  |
| ME, kcal/kg | 300 |
| CP, % | 21.5 |
| Ca, % | 1.00 |
| Available P, % | 0.45 |
| Lysine, % | 1.21 |
| Methionine, % | 0.54 |
| Met + Cys, % | 0.89 |
| Na, % | 0.20 |

TABLE 4

Dietary treatments

| Treatment | Ingredients |
|---|---|
| 1 (Control) | Corn-soy basal diet with no Se supplementation |
| 2 (SS) | Basal + 0.3 ppm Se as sodium selenite |
| 3 (SP) | Basal + 0.3 ppm Se as SEL-PLEX |
| 4 (pH 1.85) | Basal + 0.3 ppm Se as fraction precipitated at pH 1.85 |

TABLE 4-continued

Dietary treatments

| Treatment | Ingredients |
|---|---|
| 5 (pH 3.0) | Basal + 0.3 ppm Se as fraction precipitated at pH 3.0 |
| 6 (pH 4.0) | Basal + 0.3 ppm Se as fraction precipitated at pH 4.0 |
| 7 (pH 6.0) | Basal + 0.3 ppm Se as fraction precipitated at pH 6.0 |

As shown in Table 5, chickens fed diets supplemented with SGP fraction pH 4.0 or pH 6.0 accumulated almost the same quantity of selenium deposition in breast muscle tissue compared to chickens fed the SEL-PLEX (SP) supplemented diet. Compared to the control, the tissue Se level in chickens fed the SP diet and those fed with the SGP fraction pH 4.0 or pH 6.0 supplemented diets was over twice as high as chickens receiving feed supplemented with sodium selenite. Thus, the invention provides, in some embodiments, that SP, as well as SP daughter SGP fractions (e.g., pH 4.0 and pH 6.0) are bioavailable when administered to a subject (e.g., in some embodiments, SP, SGP pH 4.0 or SGP pH 6.0 are more (e.g., 2 times or more) bioavailable than inorganic selenium (e.g., sodium selenite) when administered to a subject (e.g., as evidenced by the delivery of selenium to the subject's tissue)).

TABLE 5

Effects of dietary Se sources on muscle Se concentration

| Treatment | Se, ppm |
|---|---|
| 1 - Control | 98.9$^e$ |
| 2 - SS | 137.3$^d$ |
| 3 - SP | 327.6$^a$ |
| 4 - pH 1.85 | 214.8$^c$ |
| 5 - pH 3.0 | 257.7$^b$ |
| 6 - pH 4.0 | 326.6$^a$ |
| 7 - pH 6.0 | 305.4$^a$ |

* Value with different letters indicate that the results are statistically significant (P < 0.05).

Example 4

A. Effects of Different Dietary Selenium Sources on the Gene Expression Profile in the Breast Muscle of Broilers Breast muscle tissue from chickens referenced in Example 3 was used to assess similarities and differences in gene expression profiles elicited by the following dietary treatments: Treatment 1-basal (Control); Treatment 2-Control+ 0.3 ppm sodium-selenite (SS); Treatment 3-Control+0.3 ppm SEL-PLEX; Treatment 6-0.3 ppm SGP fraction extracted from SEL-PLEX (SP) at pH 4.0. SGP fraction pH 4.0 was analyzed because it resulted in almost identical levels of selenium-deposition in breast tissue compared to that obtained with SP (See Table 5). As such, experiments were conducted during development of embodiments of the invention in order to determine if animals receiving SGP fraction pH 4.0 experienced similar in vivo effects (e.g., gene expression changes) observed in SP fed animals, or whether significant, measurable differences existed.

Animals and Tissue Sampling:

At 18-days of age, five chickens from each treatment group (described above and in Tables 3 and 4) were randomly selected and euthanized by argon asphyxiation, followed by cervical dislocation. Samples of breast muscle tissue (1 gram) were rapidly removed and flash frozen in liquid nitrogen. Samples were stored at −80° C. until analyzed.

Microarray Analysis:

Total RNA was isolated from frozen tissue using TRIZOL reagent (INVITROGEN, Carlsbad, Calif.) according to the manufacturer's protocol and purified using a RNEASY kit (QIAGEN, Valencia, Calif.). Total RNA was quantified by absorbance at 260 nm and integrity was confirmed by agarose gel electrophoresis and ethidium bromide staining of the 28S and 18S bands.

Microarray profiling was performed using the AFFYMETRIX (Santa Clara, Calif.) Genechip Chicken Genome Array following the manufacturer's suggested protocols.

Data were processed and each probe set was labeled as P (present), M (marginal) or A (absent) based the ratio of signal to noise strength using the AFFYMETRIX MAS5.0 expression summary algorithm.

Bioinformatics Analysis:

GeneSpring GX 10.0 (Silicon Genetics, Redwood, Calif.) was used to qualify and normalize microarray data and to perform statistical and gene expression pattern analyses.

To minimize the possibility of misleading findings, probe sets with low signal intensity (labeled as 'Absent' by the MAS5.0 algorithm) were excluded from further analysis. The filtered gene expression profiles were then subjected to one way ANOVA for identifying the probe sets that were differentially expressed between groups and followed by a post hoc testing to determine the genes that were significantly changed by selenium treatments when compared to Control. Only genes that differed from the Control (P≤0.05) and having a corresponding signal intensity fold change (FC)≥1.2 were deemed to be changed.

In order to visually represent the effects of dietary treatments on gene expression profiles in breast muscle tissue, 693 genes that were identified as being differentially expressed (ANOVA, P<0.05) were subjected to unsupervised hierarchical clustering based on both arrays and genes. As described in detail above, the SGP fraction pH 4.0 was directly derived from SP, and the dietary treatment groups receiving SP or the SGP fraction pH 4.0 displayed nearly identical levels of selenium deposition (bioavailability) in chicken breast muscle tissue (See Table 5, above). Thus, it was expected that both selenium treatment groups (SP and SGP fraction pH 4.0) would have displayed identical or highly similar gene expression changes. However, and quite surprisingly, a clear dietary effect on gene expression profiles was observed between the two treatment groups (See FIG. 3). Specifically, dramatic differences were observed between the gene expression profiles of the SP treatment group compared to the SGP fraction pH 4.0 treatment group, where the majority of genes analyzed responded differently to the two treatment groups. This great variation in gene expression profiles brought about by the SP treatment versus the SGP fraction pH 4.0 treatment was totally unexpected and provides heretofore unavailable insights regarding trace element biology.

For example, 693 differentially regulated genes (P<0.05, ANOVA) were subjected to unsupervised hierarchical clustering based on both arrays and genes. In the heat map shown in FIG. 3, normalized gene expression profiles are shown in colors that reflect the expression changes compared to the mean value of each gene; white, black or gray colors represent decreased, increased or no change in the level of expression intensity, respectively. The dendrogram on the top of the heat map reflects the extent of similarity in expression profiles between treatments, while the dendrogram on the left side represents the differences in the expression patterns of individual genes, across all treatments. The lengths of the dendrograms shown in FIG. 3 correspond to the level of dissimilarity between cluster leaves (a short dendrogram indicates a higher level of similarity).

Figure 4:
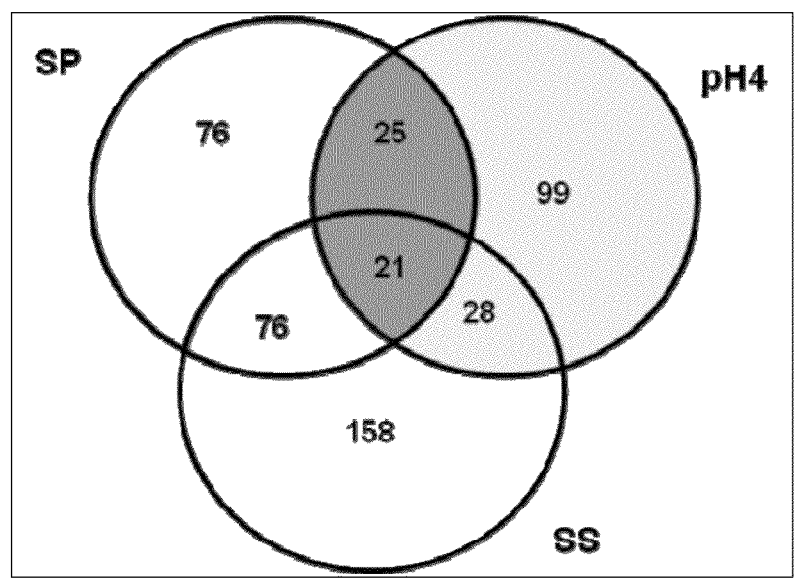
FIG. 4 shows Venn diagram depicting the different effects of SGP fraction pH 4.0 and SEL-PLEX on gene expression profiled in breast muscle.

The different effects of SGP fraction pH 4.0 and SP on gene expression profiles in breast muscle were further analyzed by comparing the number of genes significantly changed (P<0.05, FC>1.2) by SGP fraction pH 4.0 (pH4), SP and sodium selenite (SS), as represented in the Venn diagram shown in FIG. 4. There were 198, 173, and 283 significantly changed genes by SP, pH4 and SS, respectively. There were only 21 genes commonly regulated by all three Se treatment groups, and 46 commonly regulated by both SP and SGP fraction pH 4.0. There were 152 and 127 genes uniquely changed by SP or SGP fraction pH 4.0, respectively.

Figure 5:
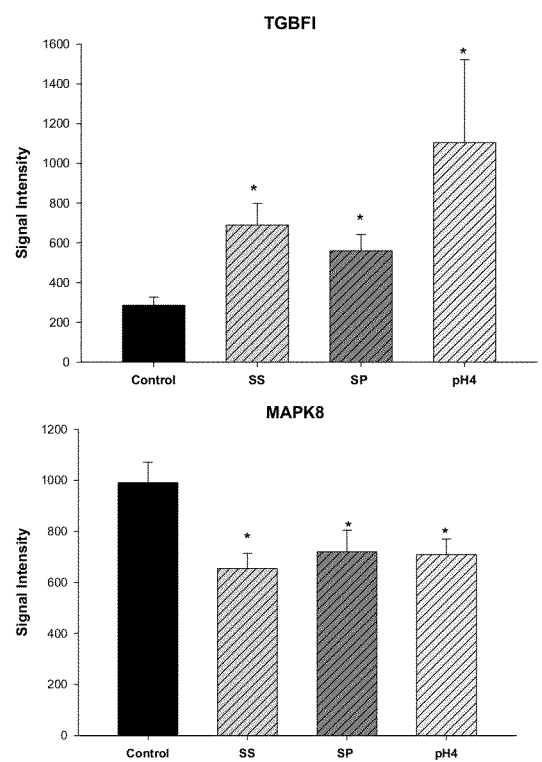
FIG. 5 shows exemplary genes identified as being commonly regulated by sodium selenite (SS), SEL-PLEX (SP) and selenoglycoprotein (SGP) fraction pH 4.0.
Figure 6:
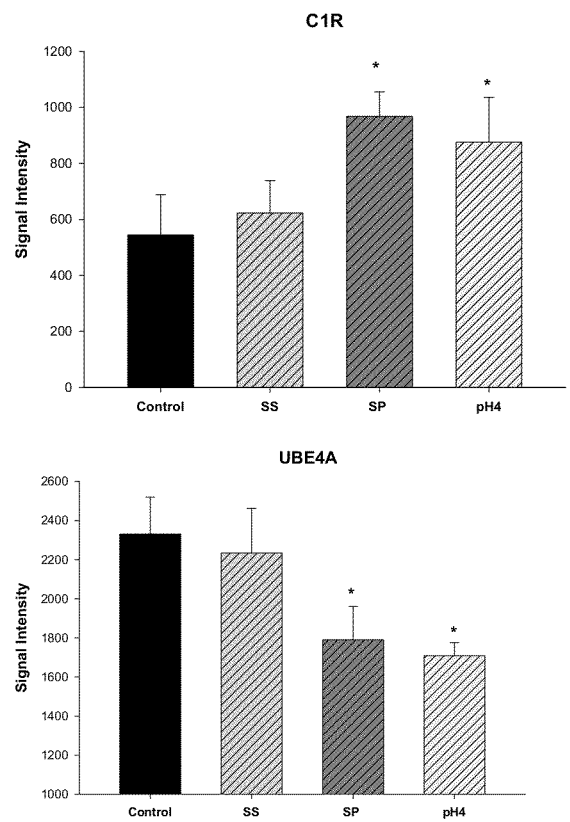
FIG. 6 shows exemplary genes identified as being commonly regulated by SEL-PLEX (SP) and selenoglycoprotein (SGP) fraction pH 4.0, but not by sodium selenite (SS).
Figure 7:
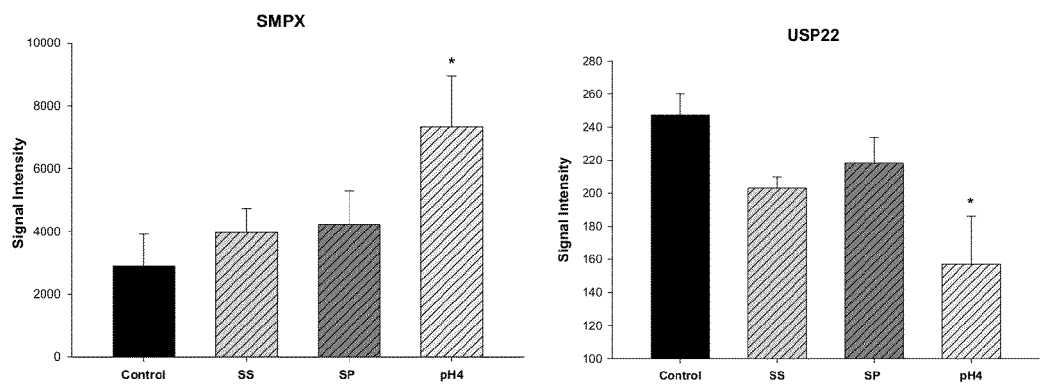
FIG. 7 shows exemplary genes identified as being uniquely regulated by selenoglycoprotein (SGP) fraction pH 4.0, and not regulated by sodium selenite (SS) or SEL-PLEX (SP).

For example, several genes identified as being differentially or commonly regulated in chicken breast muscle tissue as a result of various selenium treatments are shown in FIGS. 5-7.

Transforming growth factor, beta-induced (TGFBI 68 kDa) is thought to be involved in cell-matrix interactions, cell adhesion, migration and differentiation. Mutations of this gene have been linked to several forms of corneal dystrophies. Mitogen-activated protein kinase 8, (MAPK8, also known as JNK1) is a member of the MAP kinase family. MAP kinases act as an integration point for multiple biochemical signals, and are involved in a wide variety of cellular processes such as proliferation, differentiation, transcription regulation and development. MAPK8 also plays an important role in cellular oxidative stress response, immune response, as well as carbohydrate and protein metabolism through insulin signaling pathways. It is known that over activation of MAPK8 may induce insulin resistance through phosphorylation of Insulin receptor substrate 1 (IRS1).

FIG. 5 provides examples of genes (e.g., TGFBI and MAPK8) that were commonly regulated by SS, SP and SGP fraction pH 4.0. FIG. 6 provides examples of genes (e.g., complement component 1R (C1R), and ubiquination factor E4A (UBE4A)) commonly regulated by SP and SGP fraction pH 4.0, but not by SS. Complement component 1R (C1R) is a protein involved in the complement cascade of the innate immune system and pathogen removal. The modification of proteins with ubiquitin is an important cellular mechanism for targeting abnormal or short-lived proteins for degradation. UBE4A encodes a U-box-type ubiquitin ligase described as an E4 ubiquitination factor. UBE4A is thought to have roles in different biochemical processes other than ubiquitination, including growth and/or differentiation.

FIG. 7 provides examples of genes (e.g., small muscle protein, X-linked (SMPX) and ubiquitin specific peptidase (USP22)) that were uniquely regulated by SGP fraction pH 4.0. Small muscle protein, X-linked (SMPX) is a small protein specifically expressed in striated muscle and plays an important role in muscle contraction. Ubiquitin specific peptidase 22 (USP22) is a gene involved in ubiquitin-dependent protein catabolic processes. USP22 has been shown to be a positive-regulator of tumor growth. Increased expression of USP22 is linked to cancer progression. The ability to reduce or knockdown expression of USP22 may provide inhibition of tumor growth and/or cancer progression. For example, reducing the expression of USP22 can down-regulate the expression of Mdm2 and cyclin E, resulting in the up-regulated expression of p53 and p21, leading to cell cycling arrest and inhibition of human bladder tumor cell proliferation.

Further examination of the unique gene expression pattern elicited by the pH 4.0 fraction in muscle tissue yields additional evidence for the potential therapeutic use of the chemical forms of selenium in this fraction (e.g., to prevent or slow tumor progression and/or metastasis).

For example, the KITLG (c-KIT ligand) gene encodes the ligand of the tyrosine-kinase receptor which is a pleiotropic factor that acts in utero in germ cell and neural cell development and hematopoiesis; processes that are believed to reflect a role in cell migration. Recently, variations in the KITLG gene have been discovered which are thought to be associated with an increased risk of testicular cancer (Kanetsky et al., 2009). Furthermore, overexpression of the cognate receptor of KITLG, the KIT oncogene gene product, has been documented in chromophobe renal cell carcinoma and expression of both KITLG and KIT are known to be involved in the transformation of NIH3T3 fibroblasts and the tumorigenesis of small cell lung cancer (Yamazaki et al., 2003).

Figure 8:
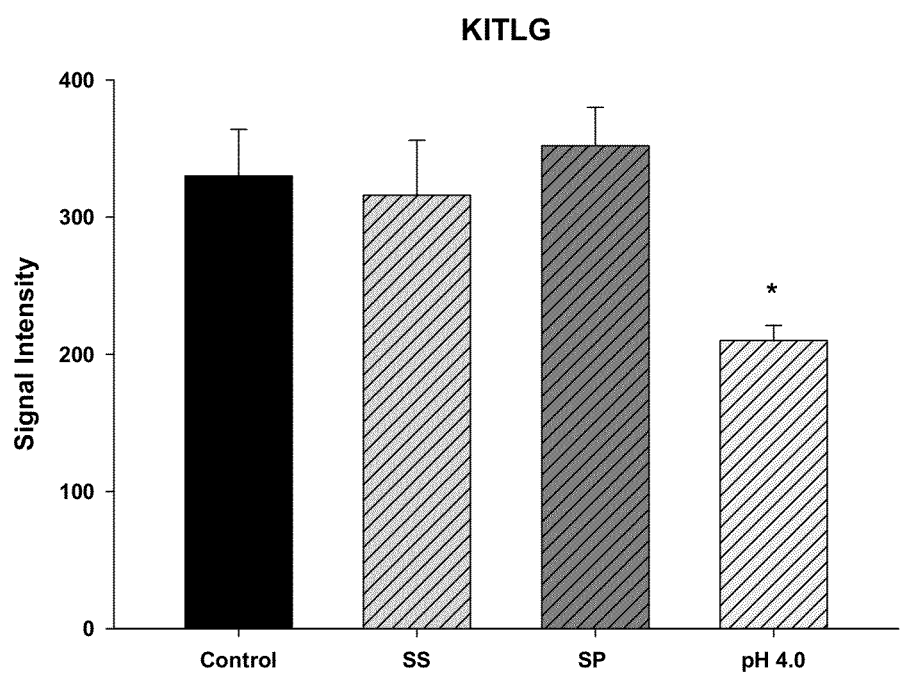
FIG. 8 shows an exemplary gene identified as being uniquely regulated by selenoglycoprotein (SGP) fraction pH 4.0, and not regulated by sodium selenite (SS) or SEL-PLEX (SP).

Surprisingly, it was observed that muscle tissue from subject administered the pH4.0 fraction significantly downregulated the KITLG gene but its level of expression was unaffected by the other selenium treatments including SP, the parent material for the pH 4.0 fraction (See, e.g., FIG. 8).

Metastasis is the primary cause of death in most human cancers and is a multistep process in which cells from the primary tumor migrate through the extracellular matrix, enter the circulation through newly formed blood vessels (tumor angiogenesis) and disseminate to distant sites (extravasation), where proliferation begins again.

Growth Factor Receptor-bound protein 2 (Grb2) is a key molecule in intracellular signal transduction. It is critical for cell cycle progression and actin-based motility and, consequently, more complex processes such as epithelial morphogenesis, angiogenesis and vasculogenesis. These important functions make Grb2 a therapeutic target for strategies designed to prevent the spread of solid tumors through local invasion and metastasis. In fact, much effort is currently directed at finding ways to blockade or antagonize Grb2 because it is felt that this may represent an effective anti-metastatic strategy (Giubellino, Burke and Bottaro, 2008).

Figure 9:
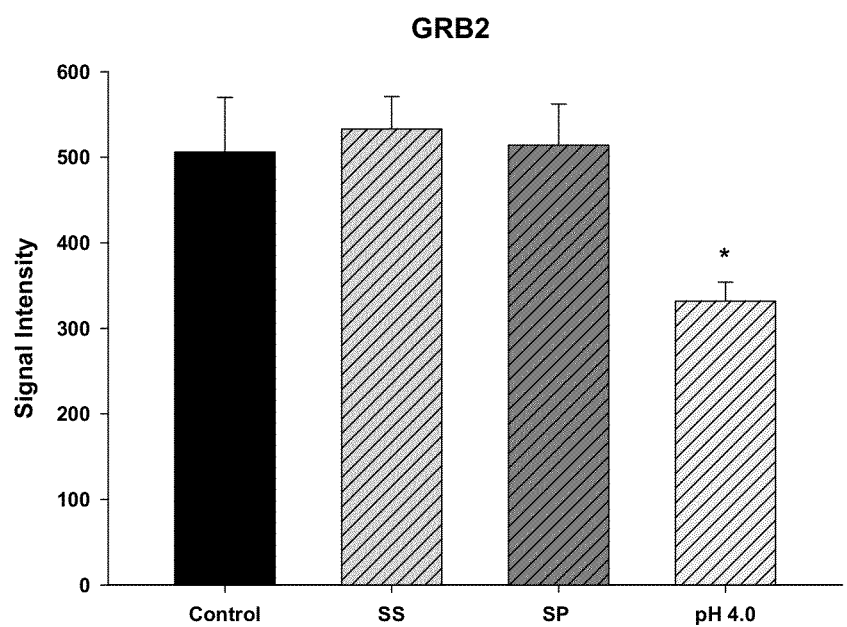
FIG. 9 shows an exemplary gene identified as being uniquely regulated by selenoglycoprotein (SGP) fraction pH 4.0, and not regulated by sodium selenite (SS) or SEL-PLEX (SP).
Figure 10:
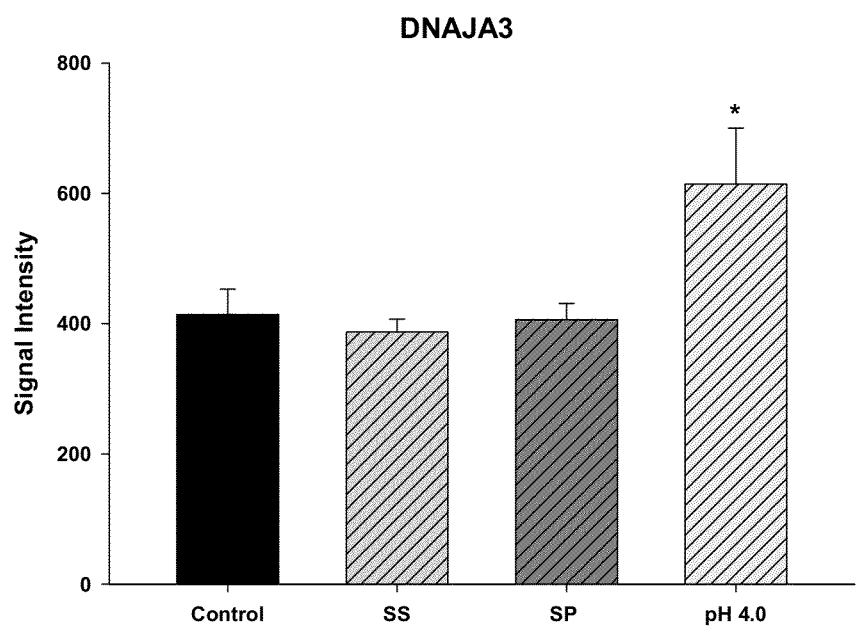
FIG. 10 shows an exemplary gene identified as being uniquely regulated by selenoglycoprotein (SGP) fraction pH 4.0, and not regulated by sodium selenite (SS) or SEL-PLEX (SP).

As shown in FIG. 9, Grb2 was significantly down regulated in pH 4.0-treated animals versus control and other selenium treatments, including sodium selenite and the parent selenium material for pH 4.0; Sel-Plex.

The potential anti-carcinogenic activity of the pH 4.0 fraction is not limited to the down-regulation of important cancer-associated genes. For example, reducing the expression of DNAJA3 in breast cancer cells has been observed to enhance their migration by allowing levels of Interleukin-8 to increase (Kim et al., 2005). This and other results strongly suggest that boosting the levels of Tid1 (DNAJA3) in cancer cells negatively regulates their motility and ability to metastasize.

DNAJA3 was robustly up-regulated in muscle tissue in experiments in response to pH 4.0 selenium (FIG. 10), but remained unresponsive, relative to control conditions, in muscle tissue from animals receiving the other selenium sources.

B. Effects of Different Selenium Treatments on Hepatic Gene Expression Profiles of Broilers In an effort to further characterize the unexpected differential gene expression effects of SP and SGP fraction pH 4.0 and to determine if the regulation of expression extended to other tissues, gene expression studies were performed as described above in Example 4(a). Instead of breast muscle tissue, liver tissue was collected and analyzed from the same chickens referenced in Example 3. In addition to SS, SP and the SGP fraction pH 4.0 supplemented treatment groups, hepatic gene expression profiles of chickens from additional treatment groups (SGP fraction pH1.85 (pH1.85), SGP fraction pH 3.0 (pH3), and SGP fraction pH 6.0 (pH6) were also characterized and compared to the control treatment group.

Figure 11:
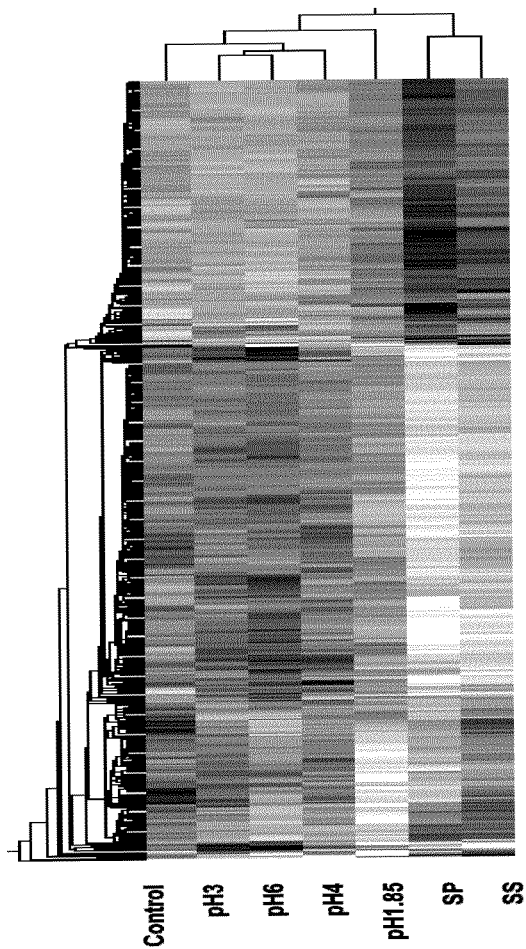
FIG. 11 shows a heat map representing the effects of different selenium-supplemented treatments described in Tables 3 and 4 of Example 3 on gene expression levels in liver tissue relative to a basal control.

Following the same experimental protocol referenced in Example 4(A), analysis of hepatic gene expression profiles from subjects of each treatment group identified 1520 genes that were significantly changed by the different dietary treatments (P<0.01, ANOVA). An unsupervised hierarchical clustering analysis of these genes is shown in FIG. 11 and provides additional evidence that treatment with different sources of selenium elicit a large degree of variation in the ability to regulate gene expression. The heat map of FIG. 11 shows normalized gene expression profiles in colors that reflect the expression changes compared to the mean value of each gene; white, black or gray colors represent decreased, increased or no change in the level of expression intensity, respectively. The dendrogram on the top of the heat map reflects the extent of similarity in expression profiles between treatments, while the dendrogram on the left side represents the differences in the expression patterns of individual genes, across all treatments. The lengths of the dendrograms shown in the figure correspond to the level of dissimilarity between cluster leaves (a short dendrogram indicates a higher level of similarity).

The differences between SP and SGP fraction pH 4.0, as well as that between SGP fraction pH 3.0 and SGP fraction pH 6.0, were dramatic, with only a few genes being commonly regulated by treatment with each of the selenium sources. In general, the effects of treatment with SGP fraction pH 1.85 on gene expression falls between SP and the other SGP treatment groups (See FIG. 11). Thus, in some embodiments, the invention provides that treatment with (e.g., diets containing and/or administration of) SEL-PLEX versus treatment with (e.g., diets containing and/or administration of) SGP fractions extracted from SEL-PLEX, result in different biological activities even though the different sources of selenium show similar effects in terms of selenium bioavailability.

Example 5

Polymersome Encapsulation of Selenoglycoproteins

A 1:1 mixture of SGPs precipitated at pH 4.0 and 6.0 (See, e.g., Examples 1 and 2) were encapsulated into polymersomes. The selenium concentration of the mixture was 3,054 ppm and contained 79.96% protein weight.

In order to generate selenoglycoprotein encapsulated polymersomes, the mixture was dissolved in aqueous buffers of pH 5.1, 6.2 and 7.4, and the suspension was mixed overnight on a shaking platform. The non-dissolved SGP was removed by centrifugation. To make polymersomes, PEO(2k)-b-PCL (12k)-based diblock copolymer was dissolved in an organic solvent (e.g. methylene chloride, tetrahydrofuran, or dimethyl sulfoxide) to yield 1 mM PEO-b-PCL polymer in organic solution. The solution was then deposited on a roughened TEFLON strip (approximately 1"×1"×1/16" thick) and placed on the bottom of a glass vial, rough side facing up. The solvent was evaporated under a vacuum at ambient temperature for 24-48 hrs, resulting in a dried film of copolymers weighing 1-10 mg.

These films were then hydrated with 2-3 ml of an aqueous solution containing a 1:1 ratio of selenoglycoproteins at pH 4.0 and pH 6.0, and then sonicated in a bath sonicator at 20-100 Hz for 1-2 hrs. After sonication was complete, vials were immediately vortexed for 1-2 min to form polymersomes that encapsulate the selenoglycoproteins in the aqueous core of PEO-b-PCL-based polymer vesicles. The polymersomes were then rapidly extruded through a polycarbonate membrane of desired pore size using a LIPOSOFAST extruder to obtain a desired average diameter of the polymersomes, in this case, ranging from 50-300 nm. Extruded polymersomes were then injected into a dialysis cassette for solution exchange against an iso-osmotic buffer of pH 7.4 for 24 hours so that all un-encapsulated selenoglycoproteins were removed.

Figure 13:
FIG. 13 shows Cryogenic Tunneling Electron Microscopy (cryo-TEM) images of polymersome encapsulated selenoglycoprotein at pH 7.4.

A sample of polymersome encapsulated selenoglycoprotein at pH 7.4 was prepared with a starting selenoglycoprotein concentration of 10 mg/ml and dialyzed against iso-osmotic PBS buffer. This sample was imaged by cryo-TEM at magnifications of 21,000× and 52,000× to obtain visual identification of successful selenoglycoprotein encapsulation inside polymersomes (See FIG. 13). Cryo-TEM allows for the imaging of specimens at cryogenic temperatures in their native hydrated states thereby preventing any undesirable conformational changes. Generally, uniform spherical polymersomes of sizes around 100 nm or slightly smaller were observed in the imaged sample. In some cases, approximately spherical aggregates of amorphous material were observed in addition to polymersomes. These aggregates may be comprised of selenoglycoprotein released from the polymersome core and which further precipitates due to the difference in pH from the inside to the outside of the polymersome by the time the samples are imaged.

The polymersome-encapsulated selenoglycoproteins at pH 5.1, 6.2 and 7.4 were further characterized by measuring selenium concentration (See Table 6). One ml of each polymersome-encapsulated selenoglycoprotein sample was freeze-dried, forming a white powder precipitate which was later weighed and inspected under 200× magnifications. Whole amounts of polymersome-encapsulated selenoglycoproteins were dissolved using concentrated acids: perchloric, nitric and hydrochloric acids, at a temperature between 100° C. to 175° C. The solutions were diluted to 50 ml using deionized (DI) water and analyzed using a MILLENIUM EXCALIBUR instrument and methodology.

TABLE 6

| | Encapsulation results | | |
|---|---|---|---|
| Formulations | Encapsulation pH | Nanocapsules (mg) | Se concentration (ppm) |
| Negative control (no selenium) | | 8.0 | 0.02 |
| 1 | 5.1 | 4.6 | 46.5 |
| 2 | 6.2 | 3.3 | 39.6 |
| 3 | 7.4 | 8.4 | 32.2 |

Example 6

Release of Selenoglycoproteins from Nanocapsules

Figure 12:
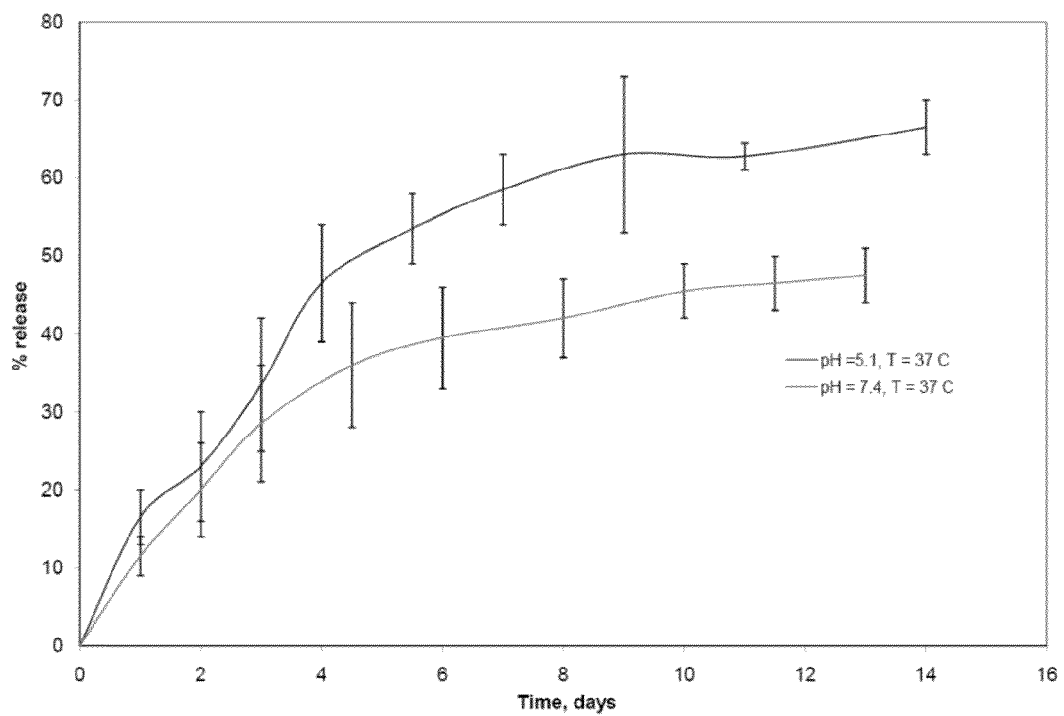
FIG. 12 depicts the release of SGP from nanocapsules at pH 5.1 and pH 7.4 over a two week period.

Release of selenoglycoprotein (SGP) from nanocapsule formulations #1 and 3 from Table 6 above, prepared with 10 mg/ml of SGP suspension and dialyzed against buffers of pH 7.4 and 5.1 respectively, was monitored over a 14-day period at 37° C. To monitor release of selenoglycoproteins from the nanocapsule-encapsulated selenoglycoprotein, dialyzed suspensions were concentrated by membrane centrifugation (centrifuge tubes with molecular weight cutoff of 300 kD were used). The concentrated suspensions were aliquoted into iso-osmolar buffers (pH of 5.1 or 7.4) and kept at 37° C. with N=2 samples for each time point. To evaluate the % release of selenoglycoprotein from the nanocapsules, the samples were centrifuged to separate intact nanocapsules at each time point. To ascertain that nanocapsules were effectively separated from the selenoglycoprotein sample, dynamic light scattering measurements were performed on separated vesicles (retentate) and free solution (filtrate) to measure particle sizes. UV absorbance of free solution were measured at 280 nm and % release of selenoglycoproteins was calculated as (Asample−Ainitial)/(Afinal−Ainitial), where Ainitial is the absorbance at day 0, and Afinal is the absorbance at the end of the study when the samples were solubilized to cause complete release (See FIG. 12). Over a 14 day period, approximately 70% of the SGP at pH 5.1 was released from the nanocapsule at steady state; whereas about 50% was released at pH 7.4. The initial release rate of SGPs at lower pH is thought to be due to acid-catalyzed hydrolysis of the nanocapsule membrane, followed by steady diffusion of selenoglycoproteins across the nanocapsules membrane. These release profiles are remarkably similar to those of doxorubicin, a cancer therapeutic, encapsulated inside PEO-b-PCL-based polymersomes (See, e.g., Ghoroghchian et al. Macromolecules, 2006, 39 (5), 1673-1675). These data confirm that encapsulation of selenoglycoproteins even at a relatively high loading concentration does not affect the release pattern in a negative way.

Example 7

Preparation of Selenoglycoproteins (SGP) Slow Release Polymers

Synthesis of polymer A. A 1:1 mixture of SGPs precipitated at pH 4.0 and 6.0 (See Example 5) was used in the preparation of SGP slow release polymers. 150 mg of SGP were dissolved in 2 ml of methacrylic acid and 1 ml of DI water. Some heating was applied to speed up dissolution. A sample of 0.5 ml of the solution was placed in a 5 ml vial containing 10 mg of AIBN, vortexed for 1 min and the air from the tube was removed under vacuum and replaced by nitrogen. The contents of the tube were polymerized by placing the tube into a laboratory oven heated to 70° C. for 2 hrs. The tube was broken and the polymer was cut into thin sections and dried at high vacuum.

Synthesis of polymer B. A mixture of: 0.064 ml of methacrylic acid, 0.091 ml of 2-hydroxyethyl-methacrylate, 1.427 ml ethylene glycol dimethacrylate and 10 mg AIBN were placed in a 5 ml vial and stirred with magnetic stirring bar, followed by 75 mg of SGP dissolved in a mixture of 1.5 ml acetic acid and 0.75 ml of DI water. The air in the vial was replaced with nitrogen and the vial was sealed and placed in an oil bath at 70° C. for four hours. The vial was broken and the polymer monolith was crushed into powder in a porcelain mortar. The volatiles were removed from the polymer under high vacuum.

SGP time release. The same, SGP slow release protocol was applied to each of the polymers (A and B). 333.7±0.1 mg of polymer was placed in a 15 ml centrifuge tube containing 5 ml of citrate buffer (pH 5.0) and the tube was gently shaken for four hours. The tubes were then centrifuged and supernatant collected while the polymer pellet was washed with two 8 ml volumes of DI water and freeze-dried. ~21 mg were taken out of the freeze-dried sample for Se analysis. The SGP extractions were repeated two more times. The weights of the samples were recorded. All of the samples lost weight during these treatments (See Tables 8 and 9).

TABLE 8

| Milligrams of polymer for release | | | | |
|---|---|---|---|---|
| Polymer | Initial | Post 1st Wash | Post 2nd Wash | Post 3rd Wash |
| A | 333.6 | 271.4 | 235.6 | 207.8 |
| B | 333.6 | 301.6 | 281.1 | 254 |

TABLE 9

| Milligrams of polymer taken for Se analysis | | | | |
|---|---|---|---|---|
| Polymer | Initial | Post 1st Wash | Post 2nd Wash | Post 3rd Wash |
| A | 21.1 | 20.5 | 20.9 | 20.6 |
| B | 20.6 | 20.5 | 20.6 | 20.8 |

To estimate concentration of the released SGP, the UV absorbance at 280 nm of the supernatants were measured and compared with the SGP calibration curve prepared in the same buffer (See Table 10).

TABLE 10

| | abs | ml in 2 ml dilution | mg SGP'S/ml in original solution | mg SGP released during interval |
|---|---|---|---|---|
| Polymer A | | | | |
| 1st wash | 0.298 | 0.1 | 0.781 | 3.907 |
| 2nd wash | 0.349 | 0.5 | 0.183 | 0.913 |
| 3rd wash | 0.353 | Not diluted | 0.046 | 0.231 |
| Polymer B | | | | |
| 1st wash | 0.35 | 0.25 | 0.366 | 1.831 |
| 2nd wash | 0.572 | Not diluted | 0.074 | 0.372 |
| 3rd wash | 0.251 | Not diluted | 0.033 | 0.165 |

The atomic absorption spectroscopy (using EXCALIBUR method and instrument) was applied to measure the concentration of residue Se in the slow release polymer (See Table 11).

TABLE 11

| Sample | Polymer A Se concentration (ppm) | Polymer B Se concentration (ppm) |
|---|---|---|
| Original sample | 318.6 | 127.1 |
| After $1^{st}$ wash | 268.8 | 116.1 |
| After $2^{nd}$ wash | 222.3 | 108.7 |
| After $3^{rd}$ wash | 215.3 | 92.3 |

According to the measurements of Se concentration in the residue pellets, 36.08% of SGP were released from Polymer A, after triple, 4 hrs washes (12 hrs total). During the same treatment 30.11% of SGP were released from Polymer B.

Example 8

Alkaline Extraction of Intracellular Yeast Proteins 200.0 g of SEL-PLEX were mixed with 1 L of 0.1M sodium hydroxide at pH11.5 and heated at 60° C. for 8 hours. The mixture was then centrifuged at 14,000×g/10 min/10° C. forming a supernatant and a pellet. The pellet was washed twice with 400 ml of DI water and freeze dried, resulting in a weight of 54.5 g (See Table 12). The supernatant at pH 11.5 and washes that were used were mixed together. The pH was reduced to 6.6 by neutralization using concentrated hydrochloric acid. Small traces of a precipitate and a clear supernatant formed during neutralization. The precipitate was separated by centrifugation and the supernatant was concentrated using AMICON 10 kDa ultrafiltration devices. The concentrate was washed with two 100 ml portions of DI water and freeze dried, yielding 64.0 g of brown solid. The remaining filtrates were combined (total volume 2l) and analyzed for selenium concentration. The separated precipitate was analyzed for Selenium and nitrogen/protein (SEE Table 12).

TABLE 12

Alkaline extraction

| | Weight (g) | Se (ppm) | Protein (w %) | Se total (mg) | Se (%) of total |
|---|---|---|---|---|---|
| SEL-PLEX | 200.0 | 1600 | 37.0 | 320.0 | 100.0 |
| Pellet after pH 11.5 extraction | 54.5 | 760 | 2.9 | 41.4 | 12.9 |
| Concentrate pH 6.6 MW > 10 kDa | 64.0 | 1918 | 52.9 | 122.8 | 38.3 |
| Filtrate 2 L MW < 10 kDa | NA (not analyzed) | 1909 | NA | 155.8 | 48.7 |

Filtrate analysis indicated a 40.7% loss of mass and 48.7% loss of selenium that was not recovered by ultra-filtration through 10 kDa membrane. β-Nucleophilic/thermal eliminations of MeSe-1 and HSe-1 and oxidized forms of these functional groups from selenium-containing peptides, resulted in degradation of the original chemical structure of SGP's and loss of mass and selenium into the filtrate. The production process commonly practiced in the art generates increased volume and heightened concentration of selenium in the filtrate which results in a waste stream that may have harmful or have deleterious effects (e.g. harmful to the environment). In contrast, the methods of the present invention provide acidic extraction and pH dependent fractionation of SGPs from selenium-enriched yeast (e.g. in a large scale commercial process). Under conditions of varying temperature, it was found that the traditional/conventional technique using alkaline hydrolysis did not work in the extraction of selenoglycoproteins from yeast cells. As described herein, extracting SGP's from yeast cells using acidic extraction was discovered to be successful.

REFERENCES

The following references are herein incorporated by reference in their entireties, as if fully set forth herein.
1. Demirci A., Pometto III A. L. 'Enhanced Organically Bound Selenium Yeast Production By Fed-Batch Fermentation' J. Agric. Food Chem. 47, 2496-2500 (1999).
2. Demirci A., Pometto III A. L. 'Production of Organically Bound Selenium Yeast by Continuous Fermentation' J. Agric. Food Chem. 47, 2491-2495 (1999).
3. Ouerdane L., Mester Z. 'Production and Characterization of Selenomethionine-Labelled *Saccharomyces cerevisiae*' J. Agric. Food Chem. 56,11792-11799, (2008).
4. Korhola. M.; Vainio, A.; Edaelman, K. 'Selenium yeast' Ann. Clin. Res. 18, 65-68, (1986).
5. Surai P. F. Natural Antioxidants in Avian Nutrition and Reproduction' Nottingham University Press 2002, 234-236 (2002).
6. Kelly, M. P.; Power R. F. 'Fractionation and identification of the major selenium compounds in selenized yeast' J. Dairy Sci. 78, 237-242 (1995).
7. McSheehy, S.; Kelly, J.; Tessier, L.; Mester, Z. 'Identification of Selenomethionine in selenized yeast using two-dimensional liquid chromatography-mass spectrometry based proteomic analysis' Analyst 130, 35-37 (2005).
8. Sedmak J. J. 'Production of beta-Glucans and Mannans' US Patent Appl. Publication Pub. No.: US 2006/0263415 A1.
9. Rayman, M. P. 'The importance of selenium to human health' The Lancet 356, 233-241 (2000).
10. McKenzie, R. C.; Rafferty, T. S.; Beckett, G. J. 'Selenium: an essential element for immune function' Trends in Immunology 19, 342-345 (1998).
11. Tapiero, H.; Townsend, D. M.; Tew, K. D. 'The antioxidant role of selenium and selenocompounds' Biomedicine & Pharmacotherapy' 57, 134-144 (2003).
12. Combs, G. F.; Grey, W. P. 'Chemopreventive Agents: Selenium' Pharmacol. Ther. 79, 179-192 (1998).
13. Clark, L. C.; Combs Jr., G. F.; Turnbull, B. W. et all. 'Effects of Selenium Supplementation for Cancer Prevention in Patients with Carcinoma of Skin' J. Am. Med. Assoc. 276, 1957-1963 (1996).
14. Otero, M. A.; Vasallo, M. C.; Verdecia, O.; Fernandez, V.; Betancourt, D. 'A Process for the Complete Fractionation of Baker's Yeast' J. Chem. Tech. Biotechnol. 66, 67-71 (1996).
15. Roberge, M. T.; Borgerding, A. J.; Finley, J. W. 'Speciation of Selenium Compounds from High Selenium Broccoli Is Affected by the Extracting Solution' J. Agric. Food Chem. 51, 4191-4197 (2003).
16. Furnsinn et al., Int. J. of Obesity and Related Metab. Dis., 19, 458-463 (1995).
17. El-Bayoumy, The role of selenium in cancer prevention, Philadelphia, Lippincott, 1-15, 1991.
18. Yu et al. Biol Trace Elem Res, 56: 117-124 (1997).
19. Yoshizawa et al., J Natl Cancer Inst, 90: 1219-1224, (1998).
20. Brooks, et al., J Urol, 166: 2034-2038, (2001).
21. Garland et al., J. Am. Coll Nutr., 12: 400-11 (1993); Ghadirian et al., Cancer Detect Prey, 24: 305-13 (2000).
22. Martin, Remington's Pharmaceutical Sciences, 15th Ed., Mack Publ. Co., Easton, Pa. (1975).
23. Goehring et al., J. Anim. Sci. 59, 725-732 (1984); Gerloff et al., J. Anim. Sci. 70, 3934-3940 (1992).
24. Meister and Anderson, Annu Rev. Biochem. 52, 711-760 (1983).
25. Deleve and Kaplowitz, Pharm. Ther. 52, 287-305 (1991).
26. Palmer and Paulson, Nutr. Rev. 55, 353-361 (1997).
27. Salonen et al., Am. J. Epidemiol. 120: 342-349 (1984).
28. Willett et al., Lancet 2: 130-134 (1983).
29. Virtamo et al., Cancer 60: 145-148 (1987).
30. Ip, J. Nutr. 128: 1845-1854 (1998).
31. Ip and Daniel, Cancer Res. 45: 61-65 (1985).
32. Pence et al., 102: 759-761 (1994).
33. Bedwal, R. S., et al., Medical Hypotheses, 41 (2):150-159 (August 1993).
34. Ferris G. M. Lloyd, et al., App. Clin. Biochem., 26:83-88 (1989).
35. Furnsinn, C. et al., Internat'l J. of Obesity and Related Metab. Dis., 19(7):458-463 (1995).
36. Mahan, Proceedings of the 15th Annual Symposium Nottingham University Press, Nottingham, UK, pp. 523-535 (1999).
37. Discher et al. Journal of Physical Chemistry B (2002), 106(11), 2848-2854.
38. Couvreur et al. Crit. Rev Ther Carrier Syst. 2002; 19(2):99-134.

39. Mosbach. Trends in Biochemical Sciences, Vol. 7, pp. 92-96, 1994.
40. Wulff. Trends in Biotechnology, Vol. 11, pp. 85-87, 1993.
41. Andersson, et al., Molecular Interactions in Bioseparations (Ngo. T. T. ed.), pp. 383-394.
31278-US-3-CIP_ST25.txt.

---

What is claimed is:

1. A composition comprising selenoglycoproteins, wherein the selenoglycoproteins contain one or more isolated fractions of acid-soluble selenoglycoproteins present in a liquid phase having a pH between 1.0 and 6.5 comprising the extract of selenium enriched yeast obtained from acidic hydrolysis of the selenium enriched yeast.

2. The composition of claim 1, wherein the one or more isolated fractions of acid-soluble selenoglycoproteins are obtained, subsequent to acidic hydrolysis of the selenium enriched yeast, via pH dependent precipitation of the selenoglycoproteins.

3. The composition of claim 2, wherein pH dependent precipitation comprises raising the pH to a level at which a portion of the selenoglycoproteins precipitate out of the liquid phase having a pH between 1.0 and 6.5 comprising the extract of selenium enriched yeast soluble under acidic conditions and collecting the precipitated selenoglycoproteins.

4. The composition of claim 3, wherein the pH level is raised to 4.0.

5. The composition of claim 3, wherein the pH level is raised to 6.0.

6. The composition of claim 1, wherein the selenoglycoproteins contain a single fraction of selenoglycoproteins recovered from the liquid phase having a pH between 1.0 and 6.5 comprising the extract of acid hydrolyzed selenium enriched yeast.

7. The composition of claim 6, wherein the single fraction of selenoglycoproteins precipitates at pH 3.0 from the liquid phase having a pH between 1.0 and 6.5 comprising the extract of acid hydrolyzed selenium enriched yeast.

8. The composition of claim 6, wherein the single fraction of selenoglycoproteins precipitates at pH 4.0 from the liquid phase having a pH between 1.0 and 6.5 comprising the extract of acid hydrolyzed selenium enriched yeast.

9. The composition of claim 6, wherein the single fraction of selenoglycoproteins precipitates at pH 6.0 from the liquid phase having a pH between 1.0 and 6.5 comprising the extract of acid hydrolyzed selenium enriched yeast.

10. The composition of claim 1, wherein the selenoglycoproteins contain two separate fractions of selenoglycoproteins recovered from the liquid phase having a pH between 1.0 and 6.5 comprising the extract of acid hydrolyzed selenium enriched yeast.

11. A composition comprising selenoglycoproteins and a carrier, wherein the selenoglycoproteins contain one or more isolated fractions of acid-soluble selenoglycoproteins present in a liquid phase having a pH between 1.0 and 6.5 comprising the extract of selenium enriched yeast obtained from acidic hydrolysis of the selenium enriched yeast.

12. The composition of claim 11, wherein the carrier is selected from the group consisting of a polymersome, a slow-release polymer, a nanocapsule, and a molecularly imprinted polymer.

13. The composition of claim 11, wherein the carrier is a slow-release polymer.

14. The composition of claim 11, wherein the carrier is a polymersome used to encapsulate selenoglycoprotein.

15. The composition of claim 14, wherein the polymersome comprises poly(ethylene oxide) (PEO) block copolymer.

16. The composition of claim 14, wherein the polymersome comprises poly(ε-caprolactone) (PCL) diblock copolymer.

17. The composition of claim 14, wherein the polymersome comprises poly(ethylene oxide)-block-poly(ε-caprolactone) (PEO-b-PCL) based diblock copolymers.

18. The composition of claim 14, wherein the polymersome is derived from the coupling of poly(lactic acid), poly(glycolide), poly(lactic-coglycolic acid) or poly(3-hydroxybutyrate) with PEO.

19. The composition of claim 14, wherein the average diameter of a polymersome encapsulating selenoglycoprotein is 50-300 nm.

* * * * *